US010975327B2

(12) United States Patent
Teixeira et al.

(10) Patent No.: US 10,975,327 B2
(45) Date of Patent: *Apr. 13, 2021

(54) HIGH PERFORMING, HIGH IMPACT BLOOM ACCORD

(71) Applicant: International Flavors & Fragrances Inc., New York, NY (US)

(72) Inventors: Miguel A. Teixeira, Oporto (PT); Masakatsu Unno, Singapore (SG); Hendrik Helweg, Huizen (NL); Lay Meng Kay, Singapore (SG); Jung Chul Shin, Singapore (SG)

(73) Assignee: INTERNATIONAL FLAVORS & FRAGRANCES INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/341,517

(22) PCT Filed: Oct. 16, 2017

(86) PCT No.: PCT/US2017/056767
§ 371 (c)(1),
(2) Date: Apr. 12, 2019

(87) PCT Pub. No.: WO2018/071897
PCT Pub. Date: Apr. 19, 2018

(65) Prior Publication Data
US 2019/0367837 A1    Dec. 5, 2019

Related U.S. Application Data

(60) Provisional application No. 62/408,350, filed on Oct. 14, 2016.

(51) Int. Cl.
| | | |
|---|---|---|
| *A61K 8/00* | (2006.01) | |
| *C11B 9/00* | (2006.01) | |
| *A61K 8/35* | (2006.01) | |
| *A61K 8/37* | (2006.01) | |
| *A61K 8/49* | (2006.01) | |
| *A61Q 5/02* | (2006.01) | |
| *C11D 3/50* | (2006.01) | |

(52) U.S. Cl.
CPC ............... *C11B 9/008* (2013.01); *A61K 8/35* (2013.01); *A61K 8/37* (2013.01); *A61K 8/498* (2013.01); *A61Q 5/02* (2013.01); *C11B 9/0019* (2013.01); *C11B 9/0034* (2013.01); *C11D 3/50* (2013.01)

(58) Field of Classification Search
CPC ...... A61K 2300/00; A61K 36/15; A61K 8/31; A61K 8/35; A61K 8/37; A61K 2800/592; A61K 8/33; A61K 8/34; A61K 8/492; C11D 3/50
See application file for complete search history.

(56) References Cited

U.S. PATENT DOCUMENTS

| | | | | |
|---|---|---|---|---|
| 5,453,276 | A * | 9/1995 | Nakatsu | A61Q 17/005 424/405 |
| 6,001,789 | A * | 12/1999 | Trinh | A61L 9/01 510/101 |
| 6,143,707 | A * | 11/2000 | Trinh | C11D 3/3907 134/25.2 |
| 6,194,362 | B1 * | 2/2001 | Trinh | C11D 1/37 510/101 |
| 9,222,055 | B2 | 12/2015 | Fraser et al. | |
| 2002/0169091 | A1 * | 11/2002 | Clare | C11D 3/3945 510/220 |
| 2005/0003957 | A1 | 1/2005 | Browne et al. | |
| 2006/0159639 | A1 | 7/2006 | Ogura et al. | |
| 2007/0280976 | A1 * | 12/2007 | Taylor | A61K 8/03 424/401 |
| 2008/0305978 | A1 * | 12/2008 | Wietfeldt | C11D 3/50 510/109 |
| 2010/0192311 | A1 * | 8/2010 | Magennis | C11D 3/48 8/142 |
| 2012/0322709 | A1 * | 12/2012 | Li | A61K 8/922 510/103 |
| 2018/0110700 | A1 * | 4/2018 | Dihora | A61K 8/31 |

FOREIGN PATENT DOCUMENTS

| | | | |
|---|---|---|---|
| EP | 1964544 B1 | 7/2017 | |
| WO | 97034987 A1 | 9/1997 | |
| WO | 99065458 A1 | 12/1999 | |
| WO | 2008090397 A1 | 7/2008 | |
| WO | WO-2008090397 A1 * | 7/2008 | ............. A61Q 19/10 |

OTHER PUBLICATIONS

Written Opinion of the International Searching Authority dated Jan. 25, 2018, International Application No. PCT/US2017/056767 filed Oct. 16, 2017, 7 pages.

\* cited by examiner

*Primary Examiner* — John R Hardee

(74) *Attorney, Agent, or Firm* — Licata & Tyrrell P.C.

(57) ABSTRACT

Disclosed are fragrance accords each containing (i) at least 7 wt % of one or more Class 1 fragrance ingredients, (ii) 5 to 85 wt % of one or more Class 2 fragrance ingredients, and (iii) 0 to 80 wt % of one or more Class 3 fragrance ingredients. The Classes 1, 2, and 3 fragrance ingredients are defined by experimental velocity. Also disclosed are delivery systems and consumer products containing such a fragrance accord.

16 Claims, No Drawings

HIGH PERFORMING, HIGH IMPACT BLOOM ACCORD

CROSS REFERENCE TO RELATED APPLICATIONS

This application is a national stage entry under 35 USC 371 for International Application No. PCT/US2017/056767, filed on Oct. 16, 2017, which claims priority to U.S. Application No. 62/408,350, filed on Oct. 14, 20162. The contents of which are incorporated herein by reference in their entirety.

BACKGROUND

All known fragrance compositions include at least one fragrance accord which is a specific combination of fragrance chemicals and, if applicable, other types of raw materials that are used to create a specific olfactive odor that cannot be created from a single fragrance ingredient or essential oil.

Fragrance compositions are used in a variety of consumer products to deliver several benefits ranging from masking unpleasant base or malodors, providing a pleasant olfactory aesthetic benefit, inducing consumer feelings (e.g., happiness, stimulation, relaxation, etc.), and implying a signal of product attributes and function (e.g., freshness, cleanliness, etc.).

Attempts have been made to design fragrance accords and fragrance compositions suitable for specific product applications that have superior or enhanced properties leading to consumer benefits. There are numerous publications teaching the selection of these fragrance ingredients based on their physical, chemical, biological or sensorial properties. For example, WO 1999/065458 defines two categories of fragrance ingredients to be formulated into high impact accords based on a combination of boiling point, partition coefficient (ClogP) and measured odor detection thresholds. These accords can be optionally encapsulated in starch to provide a boost of fragrance from a detergent powder when dispersed in water. U.S. Pat. No. 9,222,055 provides a high intensity fragrance which includes 75% to 100% of at least two key fragrance ingredients having boiling points between 100° C. and 300° C. at a pressure of 760 mmHg, molecular weights within the range of 70 atomic mass units to 175 atomic mass units, and ClogP values between 0 and 4. US 2005/0003975 also discloses perfume compositions composed of high impact accord perfume ingredients classified by boiling point, calculated CLogP, and odor detection thresholds. EP 1 964 54 describes fragrance compositions for use in consumer products to reduce allergic reactions. WO 1997/034987 discloses blooming perfume compositions for use in automatic dishwashing detergent compositions.

In spite of the many attempts described above, there is still a need to design a high performing and high impact bloom fragrance accord.

SUMMARY OF THE INVENTION

One aspect of this invention provides a high intensity bloom fragrance accord for use in a consumer product (e.g., a fabric care product) containing (i) at least 7 wt % (e.g., 7 to 95 wt %) of Class 1 fragrance ingredients, (ii) 5 to 95 wt % (e.g., 5 to 80 wt %, 10 to 80 wt %, and 10 to 70 wt %) of Class 2 fragrance ingredients, and (iii) 0 to 80 wt % of Class 3 fragrance ingredients, in which the Class 1 fragrance ingredients each have an experimental velocity of 8.5 cm/second or greater, the Class 2 fragrance ingredients each have an experimental velocity of less than 8.5 cm/second and greater than 5 cm/second, and the Class 3 fragrance ingredients each have an experimental velocity of 5 cm/second or less.

In some embodiments, the high intensity bloom fragrance accord further contains a malodor counteractive agent in an amount effective to counteracting a malodor. In other embodiments, the high intensity bloom fragrance accord is free of ingredients other than ingredients selected from Classes 1, 2, and 3 ingredients. Namely, the sum of the Class 1 fragrance ingredients, the Class 2 fragrance ingredients, and the Class 3 fragrance ingredients is 100%.

Typically, the fragrance accord comprises at least two (e.g., at least three, at least five and at least seven) Class 1 fragrance ingredients.

In some embodiments, the fragrance accord contains 20 to 100 wt % of the Class 1 and Class 2 fragrance ingredients.

Another aspect of this invention relates to a delivery system comprising one or more fragrance accords described above.

Also within the scope of this invention are bloom fragrance compositions containing by weight of the bloom fragrance composition 5% or more (e.g., 6% or more, 7% or more, 10% or more, and 20% or more) of any fragrance accord described above. These fragrance compositions typically contain at least 3% (e.g., at least 4%, at least 5%, and at least 7%) of two or more of Class 1 ingredients. The bloom fragrance accords of this invention unexpectedly improve the performance (e.g., bloom speed and fragrance intensity) of a fragrance composition.

Still within the scope of this invention relates to a consumer product comprising one or more fragrance accords of this invention, preferably at a level of 0.05 to 20 wt % by weight of the consumer product. Examples of the consumer product include a shampoo, a hair conditioner, a hair rinse, a hair refresher, a hair fixative or styling aid, a hair bleach, a hair dye or colorant, a soap such as a bar soap, a body wash, a cosmetic preparation, an all-purpose cleaner, a bathroom cleaner, a floor cleaner, a window cleaner, a bath tissue, a paper towel, a disposable wipe, a diaper rash cream or balm, a baby powder, a diaper, a bib, a baby wipe, an oral care product, a tooth paste, an oral rinse, an tooth whitener, a denture adhesive, a hand sanitizer, an anti-inflammatory balm, an anti-inflammatory ointment, an anti-inflammatory spray, a bleach, a health care device, a dental floss, a toothbrush, a tampon, a feminine napkin, a personal care product, a sunscreen lotion, a sunscreen spray, a wax-based deodorant, a glycol type deodorant, a soap type deodorant, a facial lotion, a body lotion, a hand lotion, a body powder, a shave cream, a bath soak, an exfoliating scrib, a foot cream, a facial tissue, a cleansing wipe, a fabric care product, a fabric softener, a fabric refresher, an ironing water, a liquid laundry detergent, a powder laundry detergent, a liquid dish detergent, an automatic dish detergent, a unit dose tablet or capsule, a scent booster, a drier sheet, a fine fragrance, a solid perfume, a powder foundation, a liquid foundation, an eye shadow, a lipstick or lip balm, an Eau De Toilette product, a deodorant, a rug deodorizer, a candle, a room deodorizer, a disinfectant, an aerosol antiperspirant, a stick antiperspirant, a roll-on antiperspirant, an emulsion spray antiperspirant, a clear emulsion stick antiperspirant, a soft solid antiperspirant, an emulsion roll-on antiperspirant, a clear emulsion stick antiperspirant, an opaque emulsion stick antiperspirant, a clear gel antiperspirant, a clear stick deodorant, a spray deodorant, a perfume gel, a perfume emulsion, a perfume cream, a perfume oil, a wax, a hair perfume, a cloth perfume, a deodorant perfume, a foaming bath, a bath oil, a bath salt, a bath sachet, a bath crystal, a bath tablet, a perfume jewel, a fragranced polymer, and a fragrance composition for digital devices.

The details of one or more embodiments of the invention are set forth in the description below. Other features, objects, and advantages of the invention will be apparent from the description and the claims.

DETAILED DESCRIPTION OF THE INVENTION

When a cleaning product such as a powder detergent is poured into the water, lathering begins and the consumer starts to experience the fragrance as it evaporates. Conventional bloom analysis does not focus on this stage.

Applicant has found that fragrance ingredients having a high experimental velocity (an indication of the speed of diffusivity) unexpectedly increase the performance of a fragrance accord at the lathering and bloom stage. As such, fragrance ingredients were individually tested for their experimental velocity and were divided into three classes.

Class 1 fragrance ingredients each have an experimental velocity of 8.5 cm/second or greater. Each of these fragrance ingredients typically has (i) at least eight atoms selected from the group consisting of a carbon atom, a hydrogen atom, an oxygen atom, and a nitrogen atom; (ii) a functional group selected from the group consisting of an aldehyde (—CHO), hydroxyl (—OH), olefin (C=C), ether (—O—), ester (—C(O)O—), phenyl, furanyl, and pyrazinyl groups; (iii) a vapor pressure between 0.0003 and 20 mmHg (e.g., 0.003 to 7 mmHg) at room temperature; (iv) a molecular weight within the range of 100 to 280 atomic mass units (e.g., 100 and 200 atomic mass units); and (v) a log P value between 1 and 5.5 (e.g., 1.5 to 4.5). Other suitable functional groups include ketone (R—CO—R), aromatic such as a secondary aromatic amine (Ar—NH—R), carboxylic acid (R—COOH), lactone and epoxide functional groups. In particular embodiments, the functional group is an aldehyde, aromatic or ester functional group. See, Poling, et al. (2000) The Properties of Gases and Liquids, 5th Edition, McGraw-Hill. See also U.S. Pat. Nos. 6,143,707, 6,601,789, US 2004/0138078, and EP 0888440f or additional details concerning the general physical properties of fragrance ingredients.

Class 2 fragrance ingredients each have an experimental velocity of less than 8.5 cm/second and greater than 5 cm/second. Class 3 fragrance ingredients each have an experimental velocity of 5 cm/second or less.

Experimental velocity is calculated as the distance the fragrance travels (60 cm) divided by the speed of diffusivity. The term "speed of diffusivity" refers to the time needed for olfactory detection of a fragrance ingredient measured at a distance of 60 cm from the moment when mixing, with gentle stirring at room temperature (i.e., 25° C.), 2 liters of water and 10 g of a model powder detergent containing an olfactory effective amount of the fragrance ingredient (dosed at 0.005 to 0.1 wt %). The model powder detergent does not contain any other fragrance other than the fragrance ingredient being measured.

The experimental velocity provides indication of how a fragrance ingredient performs at the lather stage and created blooming technical guidelines for consumer products including fabric care products, personal care products, and house care products. The experimental velocity measures how fast a fragrance ingredient evaporates from the water and travels to the nose. Several physical properties of the fragrance ingredient have an impact on the speed of diffusivity such as vapor pressure, molecular weight, Log P, etc.

Unexpectedly, performance at the ingredient level, accord level and total product formulation level had no correlation with previous ingredient performance studies or with known psycho-physicochemical properties and relationships between them. Rather, the speed of diffusivity of fragrance ingredients has a direct impact on the performance of a consumer product in terms of fragrance intensity and room filling capacity.

The term "room filling capacity" refers to the fragrance intensity after 10 minutes from the time when, with gentle stirring at 25° C., mixing 2 liters of water with 10 g of a model powder detergent containing an olfactory effective amount of a fragrance ingredient (dosed at 0.005 to 0.1% by weight of the model powder detergent).

Accordingly, this invention provides high intensity bloom fragrance accords for use in consumer products with enhanced speed of diffusivity, fragrance intensity and bloom/room filling, increased malodor coverage/reduction, fresh and clean fragrance sensory attributes, superior hygiene and increased sustainability.

As is conventional in the art, a "fragrance accord" refers to a mixture or blend of two or more fragrance raw materials or fragrance ingredients. A wide variety of chemicals are known in the art as fragrance ingredients, including compounds such as aldehydes, ketones and esters. More commonly, naturally occurring plant and animal oils and exudates composed of complex mixtures of various chemical components are known for use as fragrance ingredients. In this respect, the fragrance ingredients herein can be relatively simple in their compositions, composed of a single chemical, or can include highly sophisticated complex mixtures of natural and synthetic chemical components, all chosen to provide any desired odor.

In some embodiments, the fragrance accord of this invention is composed of at least 2 (e.g., at least 3, at least 4, at least 5, at least 6, and at least 7) Class 1 fragrance ingredients. In other embodiments, the fragrance accord include at least 10 fragrance ingredients selected from classes 1 and 2 fragrance ingredients, for example, at least 15, at least 20, at least 25, at least 30, at least 35, at least 40, at least 45, and/or at least 50 Classes 1 and 2 fragrance ingredients. The more fragrance raw materials that make up a fragrance accord, the more complex the fragrance accord is considered to be. For example, more simple fragrance accords include a relatively low number of fragrance raw materials, such as less than 10, less than 8, and/or less than 5 fragrance raw materials. In contrast, more complex fragrance accords include a relatively higher number of fragrance raw materials, for example, at least 25, at least 30, and/or at least 40 or more fragrance raw materials.

"Neat" or "neat oil" refers to a fragrance accord that is free from extraneous matter. A neat fragrance accord includes only fragrance ingredients and is unencapsulated and/or unbound from other compounds that would cause a delay in the release of the fragrance ingredients. In certain embodiments, the fragrance accord is a "neat fragrance accord".

The "bloom" of a fragrance accord refers to the build-up in fragrance intensity and volume that is experienced upon dissolution of a product in use. This can be either an instantaneous "burst" of perfume or a diffusive long term bloom. In accordance with the present invention, "bloom" can be assessed by experimental velocity, odor performance (e.g., fragrance intensity 25 seconds after starting the lathering phase), and/or room filling capability (e.g., fragrance intensity in a closed booth 10 minutes after starting the lathering phase). A fragrance accord with a "high intensity bloom" has an experimental velocity of 8.5 cm/second or greater, odor performance of at least 2.5 and/or room filling capability of at least 2.5 in a sensory scale from 0 to 5, with 0 indicating no smell and 5 indicating a very strong smell.

The fragrance accord of this invention typically has a bloom fragrance intensity index of at least 0.1, (e.g., at least 0.5, at least 1, 0.1 to 5, 0.2 to 4, 0.5 to 3, and 1.5). The bloom fragrance intensity index is the ratio between (i) the sensory intensity score of a fragrance accord or ingredient and (ii) the sensory intensity score of allyl amyl glycolate (AAG), as the standard. The sensory intensity score of AAG is scaled at range of 0 to 100 evaluated by a sensory panel when AAG is dissolved in an appropriate solvent (e.g. diethyl phthalate) at a concentration of 0.015%. The fragrance accord or ingredient is also evaluated by the same panel at a concentration of 0.015%. A score of 5 means that the fragrance or ingredient has a medium smell. A score of 15 indicates that the fragrance or ingredient has a medium smell. A score of 35 indicates a strong smell.

The bloom fragrance intensity score is evaluated as follows: one washed towel is placed in a small booth before the start of the evaluation in order to give enough time to saturate and reach equilibrium concentration in the volume space. The panel evaluates intensity from a window for room filling. AAG is evaluated as a standard. The bloom fragrance intensity index is then calculated as: sensory intensity score of a fragrance accord or ingredient/sensory intensity score of AAG.

Each of Class 1 and Class 2 ingredients has a bloom fragrance intensity of at least 0.1 (e.g., at least 0.2, at least 0.5, 0.1 to 5, 0.2 to 4, and 0.5 to 3).

The fragrance ingredients, standard, accords, fragrance compositions, and consumer products each can be evaluated as described above and can also be evaluated following protocols well-known in the art using different scales, which can be normalized to a scale of 0-100 for calculating the fragrance intensity index.

Each Class 1 ingredient typically has a kinetic energy of more than 5000 joules (e.g., 5001 to 50000 joules and 5500 to 25000 joules). Each Class 2 ingredient has a kinetic energy of 1400 to 5000 joules.

The kinetic energy (KE) of a molecule is calculated using its mass and velocity according to the following equation: $KE = \frac{1}{2} \times mass \times velocity^2$. Velocity is the speed of the molecule traveling in an ideal gas, whose molecules occupy negligible space and have no interactions, therefore obeying the gas laws exactly. The kinetic theory assumes that all molecules in a gas state behave ideally, which is plausible for fragrance molecules highly diluted in the air. Not to be bound by any theory, a fragrance molecule having a high kinetic energy can be easily evaporated and travel at a high speed to reach the nose when using in a consumer product.

The vapor pressure of a fragrance ingredient can be readily measured using a manometer or calculated according to the reference program EPI suite v4.00, 2000-2008 U.S. Environmental Protection Agency). Class 1 fragrance ingredients can have a vapor pressure of between 0.0002 mmHg and 20 mmHg at room temperature, wherein the lower limit of the vapor pressure may be 0.0002, 0.0005, 0.001, or 0.005 mmHg, and the upper limit of the amount may be 20, 15, 10, 15, 10, 8, and 7 mmHg at room temperature (i.e., 25° C.). Vapor pressure data for numerous fragrance ingredients are available in the literature. See, e.g., Yaws' Handbook of Thermodynamic and Physical Properties of Chemical Compounds (Norwich, N.Y., 2003).

The molecular weights of the Class 1 or 2 fragrance ingredients can vary, but are preferably within the range of 100 to 280 Dalton, wherein the lower limit of the molecular weight may be 100, 110, 120, 130, 140, 150, 160, 170, 180 or 190 Dalton and the upper limit of the molecular weight may be 280, 270, 260, 250, 240, 230, 220, 210, or 200 Dalton. In some embodiments, the Class 1 or 2 fragrance ingredients each has a molecular weight within the range of 120 to 200 Dalton.

The octanol-water partition coefficient (P) of a material, i.e., the ratio of a material's equilibrium concentration in octanol and water, is well-known in the literature as a measure of hydrophobicity and water solubility (see, Leo, et al. (1971) *Chem. Rev.* 71:526-616; Hansch, et al. (1968) *J. Org. Chem.* 33:347-350). High partition coefficient values are more conveniently given in the form of their logarithm to the base 10, log P. While log P values can be measured experimentally, i.e., directly, and measured log P data are available for many perfumes, log P values are most conveniently calculated or approximately estimated using mathematical algorithms. There are several recognized calculation or estimation methods available commercially and/or described in the literature (see, e.g., Leo (1993) *Chem. Rev.* 93(4):1281-1306). Generally these models correlate highly but may for specific materials produce log P values which differ in absolute terms (by up to 0.5 log units or even more). The log P values of many fragrance ingredients have been reported. For example, the Pomona92 database, available from Daylight Chemical Information Systems, Inc. (Irvine, Calif.) contains many, along with citations to the original literature. In accordance with the fragrance accord of this invention, the log P values of the Class 1 or 2 fragrance ingredients are at least 1.5 units. More specifically, the log P values of the Class 1 or 2 fragrance ingredients are between 1.5 and 5.5 units, wherein the lower limit may be 1.5, 1.6, 1.7, 1.8, 1.9, or 2 and the upper limit may be 5.5, 5, 4.8, 4.6, 4.5, or 4.4. In some embodiments, the Class 1 fragrance ingredients each have a log P value between 1.5 and 5.5, or more preferably between 1.7 and 4.4.

As described herein, fragrance accords were found to have a high impact bloom based upon their experimental velocity, speed of diffusivity, odor performance, and/or room filling capability. In some embodiments, a fragrance accord of this invention has one or more (e.g., at least four, at least 5, and at least 6) Class 1 fragrance ingredients with a speed of diffusivity of 7 seconds or less, as determined by the time of olfactory detection at a distance from the source of 60 cm. In addition, the fragrance accord can have one or more (e.g., at least four, at least 5, and at least 6) Class 2 fragrance ingredients with a speed of diffusivity of greater than 7 seconds and less than 12 seconds. Accordingly, the fragrance accord of this invention has a speed of diffusivity of between 0 and 12 seconds (e.g., between 0 and 8 seconds, between 0 and 6 seconds, and between 0 and 5 seconds), wherein the lower limit may be about 0, 0.5, 1, 1.5, 2, 2.5, 3, 3.5 or 4 seconds and the upper limit may be about 12, 11, 10, 9, 8, 7.5, 7, 6.5 or 6 seconds.

Non-limiting examples of Class 1 fragrance ingredients and their respective characteristics are provided in Table 1.

TABLE 1

| Ingredient | CAS No. | EV (cm/s) | KE (joules) | MW | logP |
|---|---|---|---|---|---|
| oxydibenzene | 101-84-8 | 14 | 17368 | 170.21 | 4.05 |
| 1,3,3-trimethyl-2-oxabicyclo[2.2.2]-octane | 470-82-6 | 13 | 13121 | 154.25 | 3.13 |
| (2R,4S)-2-methyl-4-propyl-1,3-oxathiane | 59323-76-1 | 13 | 12507 | 160.09 | 2.35 |
| ethyl 2-methyl-butanoate | 7452-79-1 | 12 | 9373 | 130.18 | 2.26 |
| (2R,4S)-4-methyl-2-(2-methylprop-1-en-1-yl)tetrahydro-2H-pyran | 3033-23-6 | 12 | 10268 | 154.25 | 3.58 |
| 1-methyl-4-(prop-1-en-2-yl)cyclohex-1-ene | 138-86-3 | 11 | 8409 | 136.23 | 4.83 |
| (1R,2R,4R)-ethyl bicyclo[2.2.1]hept-5-ene-2-carboxylate | — | 10 | 8894 | 166.22 | 2.81 |
| 2-isobutylthiazole | 18640-74-9 | 10 | 7053 | 141.06 | 2.9 |
| 4-methylene-2-phenyltetrahydro-2H-pyran | 60335-74-2 | 10 | 8712 | 174.24 | 3.47 |
| ethyl hexanoate | 123-66-0 | 10 | 7211 | 144.21 | 2.83 |
| 1-(5,5-dimethylcyclohex-1-en-1-yl)pent-4-en-1-one | 56973-85-4 | 10 | 9005 | 192.3 | 4.45 |
| 4,6-dimethylcyclohex-3-enecarbaldehyde | 36635-35-5 | 10 | 6268 | 138.21 | 2.85 |
| methyl benzoate | 93-58-3 | 9 | 5983 | 136.15 | 1.83 |
| 2-isopropyl-4-methylthiazole | 15679-13-7 | 9 | 5836 | 141.23 | 3 |
| 1-methoxy-4-methylbenzene | 104-93-8 | 9 | 5048 | 122.16 | 2.62 |
| ethyl 2-methyl-pentanoate | 39255-32-8 | 9 | 5959 | 144.21 | 2.76 |
| 1-methyl-4-(prop-1-en-2-yl)cyclohex-1-ene | 138-86-3 | 9 | 5629 | 136.23 | 4.83 |
| 2-isobutyl-3-methoxypyrazine | 24683-00-9 | 9 | 6471 | 166.22 | 2.86 |
| 2-(3-phenylpropyl)-pyridine | 2110-18-1 | 9 | 7247 | 197.28 | 4.04 |
| (2-methoxyethyl)-benzene | 3558-60-9 | 9 | 5003 | 136.19 | 2.27 |
| 2,6,6-trimethylbicyclo-[3.1.1]-hept-2-ene | 80-56-8 | 9 | 5004 | 136.23 | 4.27 |
| methyl 2-aminobenzoate | 134-20-3 | 9 | 5553 | 151.16 | 2.26 |
| Cypress oil | 84696-07-1 | 9.5 | 6178 | 136.23 | 4.27 |
| (3aR,8bS)-2,2,6,6,7,8,8-heptamethyl-decahydro-2H-indeno[4,5-b]-furan | — | 12 | 18724 | 264.45 | 5.52 |
| 1-(3-methylbenzo-furan-2-yl)ethan-1-one | 23911-56-0 | 10 | 8710 | 174.2 | 2.52 |

Note:
EV: Experimental velocity;
KE: Kinetic Energy;
MW: Molecular Weight

Non-limiting examples of class 2 fragrance ingredients and their respective characteristics are provided in Table 2.

TABLE 2

| Ingredients | CAS No. | EV (cm/s) | KE (joules) | MW (g/mol) | logP |
|---|---|---|---|---|---|
| (E)-4-(2,6,6-trimethylcyclohex-2-en-1-yl)but-3-en-2-one | 31798-11-5 | 8 | 6321 | 192.3 | 4.29 |
| 1-methyl-4-(propan-2-ylidene)cyclohex-1-ene | 586-62-9 | 8 | 4478 | 136.23 | 4.88 |
| (2Z,6Z)-3,7-dimethylnona-2,6-dienenitrile | 61792-11-8 | 8 | 4956 | 163.26 | 3.96 |
| octanal | 124-13-0 | 8 | 3606 | 128.21 | 2.78 |
| 2,6-dimethylhept-5-enal | 106-72-9 | 8 | 3944 | 140.22 | 3.04 |
| (1S,2R)-2,4-dimethylcyclohex-3-ene-1-carbaldehyde | 188716-52-1 | 8 | 3887 | 138.21 | 2.85 |
| (E)-dec-6-enal | — | 8 | 4338 | 154.25 | 3.55 |
| (Z)-hex-3-en-1-yl methyl carbonate | 67633-96-9 | 7 | 4235 | 158.19 | 2.47 |
| (E)-4-(2,6,6-trimethylcyclohex-1-en-1-yl)but-3-en-2-one | 79-77-6 | 7 | 5086 | 192.3 | 4.42 |
| methyl 2-methylbenzoate | 89-71-4 | 7 | 3971 | 150.17 | 2.38 |
| 2-pentylcyclopentan-1-one | 4819-67-4 | 7 | 4030 | 154.25 | 3.02 |
| 4-phenylbutan-2-one | 2550-26-7 | 7 | 3781 | 148.2 | 1.96 |
| 1-methyl-4-(prop-1-en-2-yl)cyclohex-1-ene | 138-86-3 | 7 | 3475 | 136.23 | 4.83 |
| Pine super xtreme | — | 7 | 3469 | 136 | |
| (E)-4-methyldec-3-en-5-ol | 81782-77-6 | 7 | 4243 | 170.29 | 4.05 |
| cinnamaldehyde | 14371-10-9 | 7 | 3143 | 132.16 | 1.82 |
| (1R,2R,4R)-1,7,7-trimethylbicyclo[2.2.1]heptan-2-ol | 124-76-5 | 7 | 3585 | 154.25 | 2.85 |
| (Z)-hex-3-en-1-ol | 928-96-1 | 7 | 2226 | 100.16 | 1.61 |
| 2-isopropyl-5-methylphenol | 89-83-8 | 7 | 3338 | 150.22 | 3.52 |
| (E)-undec-9-enal | 143-14-6 | 7 | 3740 | 168.28 | 4.04 |
| 2-methoxynaphthalene | 93-04-9 | 6 | 3364 | 158.2 | 3.25 |
| 1,1'-oxybis(propan-2-ol) | 110-98-5 | 6 | 2853 | 134.17 | −0.64 |
| (1S,2S)-2-(tert-butyl)cyclohexan-1-ol | 7214-18-8 | 6 | 3287 | 156.27 | 3.42 |
| 8-isopropyl-6-methylbicyclo[2.2.2]oct-5-ene-2-carbaldehyde | 68259-31-4 | 6 | 3999 | 192.15 | 4.14 |
| dodecanal | 112-54-9 | 6 | 3676 | 184.32 | 4.75 |
| p-tolyl acetate | 140-39-6 | 6 | 2933 | 150.17 | 2.14 |

TABLE 2-continued

| Ingredients | CAS No. | EV (cm/s) | KE (joules) | MW (g/mol) | logP |
|---|---|---|---|---|---|
| 1H-indole | 120-72-9 | 6 | 2194 | 117.06 | 2.1 |
| 3,7-dimethylocta-1,6-dien-3-yl acetate | 115-95-7 | 6 | 3679 | 196.29 | 4.39 |
| 3,7-dimethyloct-6-enenitrile | 51566-62-2 | 6 | 2817 | 151.25 | 3.55 |
| dodecanenitrile | 2437-25-4 | 6 | 3264 | 181.32 | 4.77 |
| (2-(1-propoxyethoxy)ethyl)benzene | 7493-57-4 | 6 | 3749 | 208.3 | 3.4 |
| 3-methyl-2-pentylcyclopent-2-en-1-one | 1128-08-1 | 6 | 2993 | 166.26 | 3.77 |
| 2,2,5,8,8,9a-hexamethyloctahydro-3aH-4a,9-methanoazuleno[5,6-d][1,3]dioxole | 211299-54-6 | 6 | 5012 | 278.43 | 5.32 |
| 3a,4,5,6,7,7a-hexahydro-1H-4,7-methanoinden-5-yl propionate | 67634-24-6 | 6 | 3569 | 206.28 | 3.34 |
| 3-(4-methylcyclohex-3-en-1-yl)butanal | 6784-13-0 | 6 | 2876 | 166.26 | 3.84 |
| (2Z,6Z)-3,7-dimethylnona-2,6-dienenitrile | 61792-11-8 | 6 | 2825 | 163.26 | 3.96 |
| 3,7-dimethylocta-1,6-dien-3-ol | 126-91-0 | 6 | 2669 | 154.25 | 3.38 |
| 2,6,6-trimethylbicyclo[3.1.1]hept-2-ene | 80-56-8 | 6 | 2357 | 136.23 | 4.27 |
| 3-(4-(tert-butyl)phenyl)-2-methylpropanal | 80-54-6 | 6 | 3535 | 204.31 | 4.36 |
| (E)-3-methyl-5-(2,2,3-trimethylcyclopent-3-en-1-yl)pent-4-en-2-ol | 67801-20-1 | 6 | 3535 | 208.34 | 4.93 |
| (E)-1-methoxy-4-(prop-1-en-1-yl)benzene | 4180-23-8 | 6 | 2514 | 148.2 | 3.39 |
| (E)-tridec-2-enenitrile | 22629-49-8 | 6 | 3156 | 193.33 | 5.04 |
| (E)-3-methyl-4-(2,6,6-trimethylcyclohex-2-en-1-yl)but-3-en-2-one | 127-51-5 | 6 | 3305 | 206.32 | 4.84 |
| 3-(4-ethylphenyl)-2,2-dimethylpropanal | 67634-15-5 | 6 | 3048 | 190.28 | 3.94 |
| (E)-trideca-3,12-dienenitrile | 134769-33-8 | 6 | 3008 | 191.31 | 4.91 |
| 2-ethoxy-4-methylphenol | 2563-07-7 | 6 | 2262 | 152.08 | 2.38 |
| benzaldehyde | 100-52-7 | 5.4 | 1523 | 106.12 | 1.71 |
| 3-methylbenzofuran-5-ol | 7182-21-0 | 5.3 | 2087 | 148.05 | 2.6 |
| hexanal | 66-25-1 | 5.3 | 1412 | 100.16 | 1.8 |
| 3a,4,5,6,7,7a-hexahydro-1H-4,7-methanoinden-5-yl isobutyrate | 67634-20-2 | 5.3 | 3051 | 220.31 | 3.76 |
| 2-((3aR,4S,5R,7S,7aR)-octahydro-1H-4,7-methanoinden-5-yl)acetaldehyde | 1339119-15-1 | 5.3 | 2469 | 178.27 | 3.01 |
| Freshness Green SUB/accord | — | 5.2 | 1851 | 136 | |
| 3,5,5-trimethylhexanal | 5435-64-3 | 5.2 | 1936 | 142.24 | 3.09 |
| 4-methoxybenzaldehyde | 123-11-5 | 5.2 | 1853 | 136.15 | 1.79 |
| ethyl isobutyrate | 97-62-1 | 5.2 | 1581 | 116.16 | 1.77 |
| (E)-3,7-dimethylocta-2,6-dien-1-yl formate | 105-86-2 | 5.2 | 2438 | 182.26 | 3.93 |
| 1-methyl-4-(prop-1-en-2-yl)cyclohex-1-ene | 138-86-3 | 5.2 | 1822 | 136.23 | 4.83 |
| (E)-3,3-dimethyl-5-(2,2,3-trimethylcyclopent-3-en-1-yl)pent-4-en-2-ol | 107898-54-4 | 5.1 | 2924 | 222.37 | 5.39 |
| 3,7-dimethyloct-6-en-1-yl acetate | 150-84-5 | 5.1 | 2563 | 198.3 | 4.56 |
| 4-allyl-2-methoxyphenol | 97-53-0 | 5.04 | 2087 | 164.2 | 2.73 |
| (3aS,4R,7S,7aR)-octahydro-1H-4,7-methanoindene-1-carbaldehyde | 30772-79-3 | 6 | 2443 | 164.24 | 2.52 |
| 1,1'-oxybis(propan-2-ol) | 110-98-5 | 8 | 3774 | 134.17 | −0.64 |
| ROSEMARY OIL | 84604-14-8 | 5.1 | 1758 | 136 | 3.13 |
| 8-methyl-1-oxaspiro(4.5)decan-2-one | 94201-19-1 | 5-8 | 1400-5000 | 168 | 1.88 |
| 2-cyclohexyl-1,6-heptadien-3-one | 313973-37-4 | 5-8 | 1400-5000 | 192 | 3.5 |

The fragrance ingredients listed in Tables 1 and 2 are readily available from commercial sources such as IFF (New York, N.Y.), Givaudan Fragrances Corp. (East Hanover, N.J.), Symrise (Branchburg, N.J.), and Firmenich (Princeton, N.J.).

The total amount of the Class 1 fragrance ingredients, i.e., component (i), of the fragrance accord constitutes at least 7% (e.g., at least 8%, at least 9%, at least 10%, at least 15%, at least 20%, 7 to 95%, 7 to 75%, and 8 to 75%) by weight of the fragrance accord, wherein the lower limit may be 7, 8, 9, 10, 15, 20, 25, 30 or 35 wt % and the upper limit may be 100, 95, 90, 80, 75, 70, 65, 60, 55, 50, 45 or 40 wt %.

The total amount of the Class 2 fragrance ingredients, i.e., component (ii), of the fragrance accord constitutes at least 5% (e.g., 5 to 95%, 5 to 90%, 5 to 85%, 5 to 80%, and 5 to 70%) by weight of the fragrance accord, wherein the lower limit may be 5, 10, 15, 20, 25, 30 or 35 wt % and the upper limit may be 95, 90, 85, 80, 75, 70, 65, 60, 55, 50, 45 or 40 wt %.

When component (i) is composed of more than one Class 1 fragrance ingredients, each Class 1 fragrance ingredient can be present at a level of between 0.02 and 99% (e.g., 0.02 to 90%, 0.02 to 80%, 0.02 to 70%, 0.02 to 50%, 0.02 to 40%, 0.02 to 30%, 0.02 to 20%, and 0.02 to 10%) based upon the weight of component (i). In some embodiments, each of the Class 1 fragrance ingredients constitutes less than 40% (e.g., less than 20%, less than 12%), 0.0001 to 10%, and 0.001 to 5%) by weight of the fragrance accord.

Likewise, when component (ii) is composed of more than one Class 2 fragrance ingredients, each Class 2 fragrance ingredient can be present at a level of 0.01 to 99% (e.g., 0.02 to 90%, 0.02 to 80%, 0.02 to 70%, 0.02 to 50%, 0.02 to 40%, 0.02 to 30%, 0.02 to 20%, and 0.02 to 10%) by weight of component (ii). In some embodiments, each of the Class 2 fragrance ingredients constitutes less than 40% (e.g., less than 30%, less than 20%, less than 12%), 0.0001 to 10%, and 0.001 to 5%) by weight of the fragrance accord.

In addition to components (i) and (ii), the fragrance accord may optionally include 0 to 80 wt % of Class 3 fragrance ingredients, wherein the lower limit may be 0, 5, 10, 15, 20, 25, 30, 35, 40, 45 or 50 wt. % and the upper limit may be 80, 75, 70, 65, 60 or 55 wt %.

Further, essential oils can be included in the fragrance accord in the amount of 0 to 30 wt % (e.g., 0 to 20 wt % and 0 to 15 wt %). Examples of suitable essential oils invention include, but are not limited to, animal fragrances such as musk oil, civet, castoreum, and ambergris; and plant fragrances such as nutmeg extract, cardomon extract, ginger extract, cinnamon extract, patchouli oil, geranium oil, orange oil, mandarin oil, orange flower extract, cedarwood, vetyver, lavandin, ylang extract, tuberose extract, sandalwood oil, bergamot oil, rosemary oil, spearmint oil, peppermint oil, lemon oil, lavender oil, citronella oil, chamomile oil (German, Maroc, or Roman), clove oil, sage oil, neroli oil, labdanum oil, *eucalyptus* oil, *verbena* oil, *mimosa* extract, *narcissus* extract, carrot seed extract, jasmine extract, fennel extract, hyssop extract, juniper extract, lemongrass extract, olibanum extract, rose extract rosemary extract, rose geranium extract, and mixtures thereof.

The fragrance accord typically contains (i) 10 to 75% top notes (e.g., 15 to 70% and 20 to 65%), (ii) 10 to 75% middle notes (e.g., 15 to 70%, 20 to 65%, and 25 to 65%), and (iii) 1 to 20 base notes (e.g., 1.5 to 15% and 2 to 10%).

The fragrance accord of the invention may also include one or more odorless solvents or oxidation inhibitors, or mixtures thereof in an amount of from 0 to 93 wt %, based on the total weight of the fragrance accord, wherein the lower limit may be 0, 5, 10, 15, 20, 25, 30, 35, 40, 45 or 50 wt. % and the upper limit may be 93, 90, 85, 80, 75, 70, 65, 60 or 55 wt. %.

Examples of an ingredient (Classes 1, 2, and 3 ingredients and other adjuvants) useful to prepare a fragrance accord include:

i) hydrocarbons, such as, for example, 3-carene, α-pinene, β-pinene, α-terpinene, γ-terpinene, p-cymene, bisabolene, camphene, caryophyllene, cedrene, farnesene, limonene, longifolene, myrcene, ocimene, valencene, (E,Z)-1,3,5-undecatriene, styrene, and diphenylmethane;

ii) aliphatic alcohols, such as, for example, hexanol, octanol, 3-octanol, 2,6-dimethyl-heptanol, 2-methyl-2-heptanol, 2-methyl-2-octanol, (E)-2-hexenol, (E)- and (Z)-3-hexenol, 1-octen-3-ol, a mixture of 3,4,5,6,6-pentamethyl-3/4-hepten-2-ol and 3,5,6,6-tetramethyl-4-methyleneheptan-2-ol, (E,Z)-2,6-nonadienol, 3,7-dimethyl-7-methoxyoctan-2-ol, 9-decenol, 10-undecenol, 4-methyl-3-decen-5-ol, aliphatic aldehydes and their acetals such as for example hexanal, heptanal, octanal, nonanal, decanal, undecanal, dodecanal, tridecanal, 2-methyloctanal, 2-methylnonanal, (E)-2-hexenal, (Z)-4-heptenal, 2,6-dimethyl-5-heptenal, 10-undecenal, (E)-4-decenal, 2-dodecenal, 2,6,10-trimethyl-5,9-undecadienal, heptanal-diethylacetal, 1,1-dimethoxy-2,2,5-trimethyl-4-hexene, and citronellyl oxyacetaldehyde;

iii) aliphatic ketones and oximes thereof, such as, for example, 2-heptanone, 2-octanone, 3-octanone, 2-nonanone, 5-methyl-3-heptanone, 5-methyl-3-heptanone oxime, 2,4,4,7-tetra-methyl-6-octen-3-one, aliphatic sulfur-containing compounds, such as for example 3-methylthio-hexanol, 3-methylthiohexyl acetate, 3-mercaptohexanol, 3-mercaptohexyl acetate, 3-mercapto-hexyl butyrate, 3-acetylthiohexyl acetate, 1-menthene-8-thiol, and aliphatic nitriles (e.g., 2-nonenenitrile, 2-tridecenenitrile, 2,12-tridecenenitrile, 3,7-dimethyl-2,6-octadienenitrile, and 3,7-dimethyl-6-octenenitrile);

iv) aliphatic carboxylic acids and esters thereof, such as, for example, (E)- and (Z)-3-hexenylformate, ethyl acetoacetate, isoamyl acetate, hexyl acetate, 3,5,5-trimethylhexyl acetate, 3-methyl-2-butenyl acetate, (E)-2-hexenyl acetate, (E)- and (Z)-3-hexenyl acetate, octyl acetate, 3-octyl acetate, 1-octen-3-yl acetate, ethyl butyrate, butyl butyrate, isoamyl butyrate, hexylbutyrate, (E)- and (Z)-3-hexenyl isobutyrate, hexyl crotonate, ethylisovalerate, ethyl-2-methyl pentanoate, ethyl hexanoate, allyl hexanoate, ethyl heptanoate, allyl heptanoate, ethyl octanoate, ethyl-(E,Z)-2,4-decadienoate, methyl-2-octinate, methyl-2-noninate, allyl-2-isoamyl oxyacetate, and methyl-3,7-dimethyl-2,6-octadienoate;

v) acyclic terpene alcohols, such as, for example, citronellol, geraniol, nerol, linalool, lavandulol, nerolidol, farnesol, tetrahydrolinalool, tetrahydrogeraniol, 2,6-dimethyl-7-octen-2-ol, 2,6-dimethyloctan-2-ol, 2-methyl-6-methylene-7-octen-2-ol, 2,6-dimethyl-5,7-octadien-2-ol, 2,6-dimethyl-3,5-octadien-2-ol, 3,7-dimethyl-4,6-octadien-3-ol, 3,7-dimethyl-1,5,7-octatrien-3-ol, 2,6-dimethyl-2,5,7-octatrien-1-ol, as well as formates, acetates, propionates, isobutyrates, butyrates, isovalerates, pentanoates, hexanoates, crotonates, tiglinates and 3-methyl-2-butenoates thereof;

vi) acyclic terpene aldehydes and ketones, such as, for example, geranial, neral, citronellal, 7-hydroxy-3,7-dimethyloctanal, 7-methoxy-3,7-dimethyloctanal, 2,6,10-trimethyl-9-undecenal, α-sinensal, β-sinensal, geranylacetone, as well as the dimethyl- and diethylacetals of geranial, neral and 7-hydroxy-3,7-dimethyloctanal;

vii) cyclic terpene alcohols, such as, for example, menthol, isopulegol, alpha-terpineol, terpinen-4-ol, menthan-8-ol, menthan-1-ol, menthan-7-ol, borneol, isoborneol, linalool oxide, nopol, cedrol, ambrinol, vetiverol, guaiol, and the formates, acetates, propionates, isobutyrates, butyrates, isovalerates, pentanoates, hexanoates, crotonates, tiglinates and 3-methyl-2-butenoates of alpha-terpineol, terpinen-4-ol, methan-8-ol, methan-1-ol, methan-7-ol, borneol, isoborneol, linalool oxide, nopol, cedrol, ambrinol, vetiverol, and guaiol;

viii) cyclic terpene aldehydes and ketones, such as, for example, menthone, isomenthone, 8-mercaptomenthan-3-one, carvone, camphor, fenchone, α-ionone, β-ionone, α-n-methylionone, β-n-methylionone, α-isomethylionone, β-isomethylionone, alpha-irone, α-damascone, β-damascone, β-damascenone, δ-damascone, γ-damascone, 1-(2,4,4-trimethyl-2-cyclohexen-1-yl)-2-buten-1-one, 1,3,4,6,7,8a-hexahydro-1,1,5,5-tetramethyl-2H-2,4a-methanonaphthalen-8(5H-)-one, nootkatone, dihydronootkatone; acetylated cedarwood oil (cedryl methyl ketone);

ix) cyclic alcohols, such as, for example, 4-tert-butylcyclohexanol, 3,3,5-trimethylcyclo-hexanol, 3-isocamphylcyclohexanol, 2,6,9-trimethyl-Z2,Z5,E9-cyclododecatrien-1-ol, 2-iso-butyl-4-methyltetrahydro-2H-pyran-4-ol;

x) cycloaliphatic alcohols, such as, for example, alpha,3,3-trimethylcyclo-hexylmethanol, 2-methyl-4-(2,2,3-trimethyl-3-cyclopent-1-yl)butanol, 2-methyl-4-(2,2,3-trimethyl-3-cyclopent-1-yl)-2-buten-1-ol, 2-ethyl-4-(2,2,3-trimethyl-3-cyclopent-1-yl)-2-buten-1-ol, 3-methyl-5-(2,2,3-trimethyl-3-cyclopent-1-yl)-pentan-2-ol, 3-methyl-5-(2,2,3-trimethyl-3-cyclopent-1-yl)-4-penten-2-ol, 3,3-dimethyl-5-(2,2,3-trimethyl-3-cyclopent-1-yl)-4-penten-2-ol, 1-(2,2,6-trimethylcyclohexyl)pentan-3-ol, 1-(2,2,6-trimethylcyclohexyl)hexan-3-ol;

xi) cyclic and cycloaliphatic ethers, such as, for example, cineole, cedryl methyl ether, cyclododecyl methyl ether;

xii) (ethoxymethoxy)cyclododecane; alpha-cedrene epoxide, 3a,6,6,9a-tetramethyl-dodecahydronaphtho[2,1-b]furan, 3a-ethyl-6,6,9a-trimethyldodecahydronaphtho[2,1-b]furan, 1,5,9-trimethyl-13-oxabicyclo[10.1.0]-trideca-4,8-diene, rose oxide, 2-(2,4-dimethyl-3-cyclohexen-1-yl)-5-methyl-5-(1-methylpropyl)-1,3-dioxan-;

xiii) cyclic ketones, such as, for example, 4-tert.-butyl-cyclohexanone, 2,2,5-trimethyl-5-pentylcyclopentanone, 2-heptylcyclopentanone, 2-pentylcyclopentanone, 2-hydroxy-3-methyl-2-cyclopenten-1-one, 3-methyl-cis-2-penten-1-yl-2-cyclopenten-1-one, 3-methyl-2-pentyl-2-cyclopenten-1-one, 3-methyl-4-cyclopentadecenone, 3-methyl-5-cyclopentadecenone, 3-methylcyclopentadecanone, 4-(1-ethoxyvinyl)-3,3,5,5-tetramethylcyclohexanone, 4-tert.-pentylcyclohexanone, 5-cyclohexadecen-1-one, 6,7-dihydro-1,1,2,3,3-pentamethyl-4(5H)-indanone, 5-cyclohexadecen-1-one, 8-cyclohexadecen-1-one, 9-cycloheptadecen-1-one, cyclopentadecanone, cycloaliphatic aldehydes, such as, for example, 2,4-dimethyl-3-cyclohexene carbaldehyde, 2-methyl-4-(2,2,6-trimethyl-cyclohexen-1-yl)-2-butenal, 4-(4-hydroxy-4-methylpentyl)-3-cyclohexene carbaldehyde, 4-(4-methyl-3-penten-1-yl)-3-cyclohexene carbaldehyde;

xiv) cycloaliphatic ketones, such as, for example, 1-(3,3-dimethylcyclohexyl)-4-penten-1-one, 1-(5,5-dimethyl-1-cyclohexen-1-yl)-4-penten-1-one, 2,3,8,8-tetramethyl-1,2,3,4,5,6,7,8-octahydro-2-naphtalenyl methyl-ketone, methyl-2,6,10-trimethyl-2,5,9-cyclododecatrienyl ketone, tert.-butyl-(2,4-dimethyl-3-cyclohexen-1-yl)ketone;

xv) esters of cyclic alcohols, such as, for example, 2-tert.-butylcyclohexyl acetate, 4-tert-butylcyclohexyl acetate, 2-tert-pentylcyclohexyl acetate, 4-tert-pentylcyclohexyl acetate, decahydro-2-naphthyl acetate, 3-pentyltetrahydro-2H-pyran-4-yl acetate, decahydro-2,5,5,8a-tetramethyl-2-naphthyl acetate, 4,7-methano-3a,4,5,6,7,7a-hexahydro-5 or 6-indenyl acetate, 4,7-methano-3a,4,5,6,7,7a-hexahydro-5 or 6-indenyl propionate, 4,7-methano-3a,4,5,6,7,7a-hexahydro-5 or 6-indenyl-isobutyrate, 4,7-methanooctahydro-5 or 6-indenyl acetate;

xvi) esters of cycloaliphatic carboxylic acids, such as, for example, allyl 3-cyclohexyl-propionate, allyl cyclohexyl oxyacetate, methyl dihydrojasmonate, methyl jasmonate, methyl 2-hexyl-3-oxocyclopentanecarboxylate, ethyl 2-ethyl-6,6-dimethyl-2-cyclohexenecarboxylate, ethyl 2,3,6,6-tetramethyl-2-cyclohexenecarboxylate, ethyl 2-methyl-1,3-dioxolane-2-acetate;

xvii) aromatic and aliphatic alcohols, such as, for example, benzyl alcohol, 1-phenylethyl alcohol, 2-phenylethyl alcohol, 3-phenylpropanol, 2-phenylpropanol, 2-phenoxyethanol, 2,2-dimethyl-3-phenylpropanol, 2,2-dimethyl-3-(3-methylphenyl)propanol, 1,1-dimethyl-2-phenylethyl alcohol, 1,1-dimethyl-3-phenylpropanol, 1-ethyl-1-methyl-3-phenylpropanol, 2-methyl-5-phenylpentanol, 3-methyl-5-phenylpentanol, 3-phenyl-2-propen-1-ol, 4-methoxybenzyl alcohol, 1-(4-isopropylphenyl)ethanol;

xviii) esters of aliphatic alcohols and aliphatic carboxylic acids, such as, for example, benzyl acetate, benzyl propionate, benzyl isobutyrate, benzyl isovalerate, 2-phenylethyl acetate, 2-phenylethyl propionate, 2-phenylethyl isobutyrate, 2-phenylethyl isovalerate, 1-phenylethyl acetate, α-trichloromethylbenzyl acetate, α,α-dimethylphenylethyl acetate, alpha, alpha-dimethylphenylethyl butyrate, cinnamyl acetate, 2-phenoxyethyl isobutyrate, 4-methoxybenzyl acetate, araliphatic ethers, such as for example 2-phenylethyl methyl ether, 2-phenylethyl isoamyl ether, 2-phenylethyl-1-ethoxyethyl ether, phenylacetaldehyde dimethyl acetal, phenylacetaldehyde diethyl acetal, hydratropaaldehyde dimethyl acetal, phenylacetaldehyde glycerol acetal, 2,4,6-trimethyl-4-phenyl-1,3-dioxane, 4,4a,5,9b-tetrahydroindeno[1,2-d]-m-dioxin, 4,4a,5,9b-tetrahydro-2,4-dimethylindeno[1,2-d]-m-dioxin;

xix) aromatic and aliphatic aldehydes, such as, for example, benzaldehyde; phenylacetaldehyde, 3-phenylpropanal, hydratropaldehyde, 4-methylbenzaldehyde, 4-methylphenyl-acetaldehyde, 3-(4-ethylphenyl)-2,2-dimethylpropanal, 2-methyl-3-(4-isopropylphenyl)propanal, 2-methyl-3-(4-tert.-butylphenyl)propanal, 3-(4-tert.-butylphenyl)propanal, cinnamaldehyde, alpha-butylcinnamaldehyde, alpha-amylcinnamaldehyde, alpha-hexylcinnamaldehyde, 3-methyl-5-phenylpentanal, 4-methoxybenzaldehyde, 4-hydroxy-3-methoxybenzaldehyde, 4-hydroxy-3-ethoxybenzaldehyde, 3,4-methylene-dioxybenzaldehyde, 3,4-dimethoxybenzaldehyde, 2-methyl-3-(4-methoxyphenyl)propanal, 2-methyl-3-(4-methylendioxyphenyl)propanal;

xx) aromatic and aliphatic ketones, such as, for example, acetophenone, 4-methylaceto-phenone, 4-methoxyacetophenone, 4-tert.-butyl-2,6-dimethylacetophenone, 4-phenyl-2-butanone, 4-(4-hydroxyphenyl)-2-butanone, 1-(2-naphthalenyl)ethanone, benzophenone, 1,1,2,3,3,6-hexamethyl-5-indanyl methyl ketone, 6-tert.-butyl-1,1-dimethyl-4-indanyl methyl ketone, 1-[2,3-dihydro-1,1,2,6-tetramethyl-3-(1-methyl-ethyl)-1H-5-indenyl]ethanone, 5',6',7',8'-tetrahydro-3',5',5',6',8',8'-hexamethyl-2-acetonaphthone;

xxi) aromatic and araliphatic carboxylic acids and esters thereof, such as, for example, benzoic acid, phenylacetic acid, methyl benzoate, ethyl benzoate, hexyl benzoate, benzyl benzoate, methyl phenylacetate, ethyl phenylacetate, geranyl phenylacetate, phenylethyl phenylacetate, methyl cinnamate, ethyl cinnamate, benzyl cinnamate, phenylethyl cinnamate, cinnamyl cinnamate, allyl phenoxyacetate, methyl salicylate, isoamyl salicylate, hexyl salicylate, cyclohexyl salicylate, cis-3-hexenyl salicylate, benzyl salicylate, phenylethyl salicylate, methyl 2,4-dihydroxy-3,6-dimethylbenzoate, ethyl 3-phenylglycidate, ethyl 3-methyl-3-phenylglycidate;

xxii) nitrogen-containing aromatic compounds, such as, for example, 2,4,6-trinitro-1,3-dimethyl-5-tert-butylbenzene, 3,5-dinitro-2,6-dimethyl-4-tert-butylacetophenone, cinnamonitrile, 5-phenyl-3-methyl-2-pentenonitrile, 5-phenyl-3-methylpentanonitrile, methyl anthranilate, methy-N-methylanthranilate, Schiff's bases of methyl anthranilate with 7-hydroxy-3,7-dimethyl-octanal, 2-methyl-3-(4-tert.-butylphenyl)propanal or 2,4-dimethyl-3-cyclohexene carbaldehyde, 6-isopropylquinoline, 6-isobutylquinoline, 6-sec-butylquinoline, indole, skatole, 2-methoxy-3-isopropylpyrazine, 2-isobutyl-3-methoxypyrazine;

xxiii) phenols, phenyl ethers and phenyl esters, such as, for example, estragole, anethole, eugenol, eugenyl methyl ether, isoeugenol, isoeugenol methyl ether, thymol, carvacrol, diphenyl ether, beta-naphthyl methyl ether, beta-naphthyl ethyl ether, beta-naphthyl isobutyl ether, 1,4-dimethoxybenzene, eugenyl acetate, 2-methoxy-4-methylphenol, 2-ethoxy-5-(1-propenyl)phenol, p-cresyl phenylacetate;

xxiv) heterocyclic compounds, such as, for example, 2,5-dimethyl-4-hydroxy-2H-furan-3-one, 2-ethyl-4-hydroxy-5-methyl-2H-furan-3-one, 3-hydroxy-2-methyl-4H-pyran-4-one, 2-ethyl-3-hydroxy-4H-pyran-4-one;

xxv) lactones, such as, for example, 1,4-octanolide, 3-methyl-1,4-octanolide, 1,4-nonanolide, 1,4-decanolide, 8-decen-1,4-olide, 1,4-undecanolide, 1,4-dodecanolide, 1,5-decanolide, 1,5-dodecanolide, 1,15-pentadecanolide, cis- and trans-11-pentadecen-1,15-olide, cis- and trans-12-pentadecen-1,15-olide, 1,16-hexadecanolide, 9-hexadecen-1,16-olide, 10-oxa-1,16-hexadecanolide, 11-oxa-1,16-hexadecanolide, 12-oxa-1,16-hexadecanolide, ethylene-1,12-dodecanedioate, ethylene-1,13-tridecanedioate, coumarin, 2,3-dihydrocoumarin, and octahydrocoumarin;

xxvi) essential oils, concretes, absolutes, resins, resinoids, balsams, tinctures such as for example ambergris tincture, amyris oil, *angelica* seed oil, *angelica* root oil, aniseed oil, valerian oil, basil oil, tree moss absolute, bay oil, armoise oil, benzoe resinoid, bergamot oil, beeswax absolute, birch tar oil, bitter almond oil, savory oil, buchu leaf oil, cabreuva oil, cade oil, calamus oil, camphor oil, *cananga* oil, cardamom oil, cascarilla oil, *cassia* oil, cassie absolute, castoreum absolute, cedar leaf oil, cedar wood oil, cistus oil, citronella oil, lemon oil, copaiba balsam, copaiba balsam oil, coriander oil, costus root oil, cumin oil, cypress oil, davana oil, dill weed oil, dill seed oil, eau de brouts absolute, oakmoss absolute, elemi oil, estragon oil, *eucalyptus citriodora* oil, *eucalyptus* oil (cineole type), fennel oil, fir needle oil, *galbanum* oil, *galbanum* resin, geranium oil, grapefruit oil, guaiacwood oil, gurjun balsam, gurjun balsam oil, helichrysum absolute, helichrysum oil, ginger oil, iris root absolute, iris root oil, jasmine absolute, calamus oil, blue camomile oil, Roman camomile oil, carrot seed oil, cascarilla oil, pine needle oil, spearmint oil, caraway oil, labdanum oil, labdanum absolute, labdanum resin, lavandin absolute, lavandin oil, lavender absolute, lavender oil, lemongrass oil, lovage oil, lime oil distilled, lime oil expressed, linaloe oil, *Litsea cubeba* oil, laurel leaf oil, mace oil, marjoram oil, mandarin oil, massoi (bark) oil, *mimosa* absolute, ambrette seed oil, musk tincture, clary sage oil, nutmeg oil, myrrh absolute, myrrh oil, myrtle oil, clove leaf oil, clove bud oil, neroli oil, olibanum absolute, olibanum oil, opopanax oil, orange flower absolute, orange oil, *origanum* oil, palmarosa oil, patchouli oil, *perilla* oil, Peru balsam oil, parsley leaf oil, parsley seed oil, petitgrain oil, peppermint oil, pepper oil, pimento oil, pine oil, pennyroyal oil, rose absolute, rosewood oil, rose oil, rosemary oil, Dalmatian sage oil, Spanish sage oil, sandal-wood oil, celery seed oil: spike-lavender oil, star anise oil, storax oil, *tagetes* oil, fir needle oil, tea tree oil, turpentine oil, thyme oil, Tolu balsam, tonka bean absolute, tuberose absolute, vanilla extract, violet leaf absolute, *verbena* oil, vetiver oil, juniperberry oil, wine lees oil, wormwood oil, wintergreen oil, ylang-ylang oil, hyssop oil, civet absolute, cinnamon leaf oil, cinnamon bark oil, and fractions thereof or ingredients isolated therefrom;

(xxvii) flavors including, but are not limited to, acetaldehyde, dimethyl sulfide, ethyl acetate, ethyl propionate, methyl butyrate, and ethyl butyrate. Flavors containing volatile aldehydes or esters include, e.g., cinnamyl acetate, cinnamaldehyde, citral, diethylacetal, dihydrocarvyl acetate, eugenyl formate, and p-methylanisole. Further examples of volatile compounds that may be present in the instant flavor oils include acetaldehyde (apple); benzaldehyde (cherry, almond); cinnamic aldehyde (cinnamon); citral, i.e., alpha citral (lemon, lime); neral, i.e., beta citral (lemon, lime); decanal (orange, lemon); ethyl vanillin (vanilla, cream); heliotropine, i.e., piperonal (vanilla, cream); vanillin (vanilla, cream); alpha-amyl cinnamaldehyde (spicy fruity flavors); butyraldehyde (butter, cheese); valeraldehyde (butter, cheese); citronellal (modifies, many types); decanal (citrus fruits); aldehyde C-8 (citrus fruits); aldehyde C-9 (citrus fruits); aldehyde C-12 (citrus fruits); 2-ethyl butyraldehyde (berry fruits); hexenal, i.e., trans-2 (berry fruits); tolyl aldehyde (cherry, almond); veratraldehyde (vanilla); 2,6-dimethyl-5-heptenal, i.e., melonal (melon); 2-6-dimethyloctanal (green fruit); and 2-dodecenal (citrus, mandarin); cherry; or grape and mixtures thereof. The composition may also contain taste modulators and artificial sweeteners. As used herein, flavor is understood to include spice oleoresins derived from allspice, basil, *capsicum*, cinnamon, cloves, cumin, dill, garlic, marjoram, nutmeg, paprika, black pepper, rosemary, and turmeric, essential oils, anise oil, caraway oil, clove oil, *eucalyptus* oil, fennel oil, garlic oil, ginger oil, peppermint oil, onion oil, pepper oil, rosemary oil, spearmint oil, citrus oil, orange oil, lemon oil, bitter orange oil, tangerine oil, alliaceous flavors, garlic, leek, chive, and onion, botanical extracts, *arnica* flower extract, chamomile flower extract, hops extract, marigold extract, botanical flavor extracts, blackberry, chicory root, cocoa, coffee, kola, licorice root, rose hips, sarsaparilla root, *sassafras* bark, tamarind and vanilla extracts, protein hydrolysates, hydrolyzed vegetable proteins, meat protein hydrolyzes, milk protein hydrolyzates and compounded flavors both natural and artificial including those disclosed in S. Heath, Source Book of Flavors, Avi Publishing Co., Westport Conn., 1981, pages 149-277. Specific preferred flavor adjuvants include, but are not limited to, the following: anise oil; ethyl-2-methyl butyrate; vanillin; cis-3-heptenol; cis-3-hexenol; trans-2-heptenal; butyl valerate; 2,3-diethyl pyrazine; methylcyclo-pentenolone; benzaldehyde; valerian oil; 3,4-dimeth-oxyphenol; amyl acetate; amyl cinnamate, y-butyryl lactone; furfural; trimethyl pyrazine; phenyl acetic acid; isovaleraldehyde; ethyl maltol; ethyl vanillin; ethyl valerate; ethyl butyrate; cocoa extract; coffee extract; peppermint oil; spearmint oil; clove oil; anethol; cardamom oil; wintergreen oil; cinnamic aldehyde; ethyl-2-methyl valerate; g-hexenyl lactone; 2,4-decadienal; 2,4-heptadienal; methyl thiazole alcohol (4-methyl-5-b-hydroxyethyl thiazole); 2-methyl butanethiol; 4-mercapto-2-butanone; 3-mercapto-2-pentanone; 1-mercapto-2-propane; benzaldehyde; furfural; furfuryl alcohol; 2-mercapto propionic acid; alkyl pyrazine; methyl pyrazine; 2-ethyl-3-methyl pyrazine; tetramethyl pyrazine; polysulfides; dipropyl disulfide; methyl benzyl disulfide; alkyl thiophene; 2,3-dimethyl thiophene; 5-methyl furfural; acetyl furan; 2,4-decadienal; guiacol; phenyl acetaldehyde; b-decalactone; d-limonene; acetoin; amyl acetate; maltol; ethyl butyrate; levulinic acid; piperonal; ethyl acetate; n-octanal; n-pentanal; n-hexanal; diacetyl; monosodium glutamate; monopotassium glutamate; sulfur-containing amino acids, e.g., cysteine; hydrolyzed vegetable protein; 2-methylfuran-3-thiol; 2-methyldihydrofuran-3-thiol; 2,5-dimethylfuran-3-thiol; hydrolyzed fish protein; tetramethyl pyrazine; propylpropenyl disulfide; propylpropenyl trisulfide; diallyl disulfide; diallyl trisulfide; dipropenyl disulfide; dipropenyl trisulfide; 4-methyl-2-[(methylthio)-ethyl]-1,3-dithio lane; 4,5-dimethyl-2-(methylthiomethyl)-1,3-dithiolane; 4-methyl-2-(methylthiomethyl)-1,3-dithiolane, and the flavor ingredients described in U.S. Pat. Nos. 6,110,520 and 6,333,180;

(xxviii) malodor counteracting agents including an α,β-unsaturated carbonyl compounds including but not limited to those disclosed in U.S. Pat. No. 6,610,648 and EP 2,524,704, amyl cinnamaldehyde, benzophenone, benzyl benzoate, benzyl isoeugenol, benzyl phenyl acetate, benzyl salicylate, butyl cinnamate, cinnamyl butyrate, cinnamyl isovalerate, cinnamyl propionate, decyl acetate, ethyl myristate, isobutyl cinnamate, isoamyl salicylate, phenethyl benzoate, phenethyl phenyl acetate, triethyl citrate, tripropylene glycol n-butyl ether, isomers of bicyclo[2.2.1]hept-5-ene-2-carboxylic acid, ethyl ester, nano silver, zinc undecenylate, β-naphthyl methyl ether, β-naphthyl ketone, benzyl acetone. They may include mixture of hexahydro-4,7-methanoinden-5-yl propionate and hexahydro-4,7-methanoinden-6-yl propionate; 4-(2,6,6-trimethyl-2-cyclohexen-1-yl)-3-methyl-3-buten-2-one; 3,7-dimethyl-2,6-nonadien-1-nitrile; dodecahydro-3a,6,6,9a-tetramethylnaphtho (2,1-b) furan; ethylene glycol cyclic ester of n-dodecanedioic acid; 1-cyclohexadecen-6-one; 1-cycloheptadecen-10-one; and corn mint oil. They may also include 1-cyclohexylethan-1-yl butyrate; 1-cyclohexylethan-1-yl acetate; 1-cyclohexylethan-1-ol; 1-(4'-methylethyl)cyclohexylethan-1-yl propionate; and 2'-hydroxy-1'-ethyl(2-phenoxy)acetate each of which compound is marketed under the trademark VEILEX by International Flavors & Fragrances Inc. More suitable malodor counteracting agents are polymers containing an a-keto, benzaldehyde, or α,β-unsaturated carbonyl moiety, such as those described in US Application Publications 2012/0294821, 2013/0101544 and 2013/0101545;

(xxix) vitamins including any vitamin, a derivative thereof and a salt thereof. Examples are as follows: vitamin A and its analogs and derivatives (e.g., retinol, retinal, retinyl palmitate, retinoic acid, tretinoin, and iso-tretinoin, known collectively as retinoids), vitamin E (tocopherol and its derivatives), vitamin C (L-ascorbic acid and its esters and other derivatives), vitamin B3 (niacinamide and its derivatives), alpha hydroxy acids (such as glycolic acid, lactic acid, tartaric acid, malic acid, citric acid, etc.) and beta hydroxy acids (such as salicylic acid and the like);

(xxx) antibacterials including bisguanidines (e.g., chlorhexidine digluconate), diphenyl compounds, benzyl alcohols, trihalocarbanilides, quaternary ammonium compounds, ethoxylated phenols, and phenolic compounds, such as halo-substituted phenolic compounds, like PCMX (i.e., p-chloro-m-xylenol), triclosan (i.e., 2, 4, 4'-trichloro-2' hydroxy-diphenylether), thymol, and triclocarban;

(xxxi) antioxidants such as beta-carotene, vitamin C (Ascorbic Acid) or an ester thereof, vitamin A or an ester thereof, vitamin E or an ester thereof, lutein or an ester thereof, lignan, lycopene, selenium, flavonoids, vitamin-like antioxidants such as coenzyme Q10 (CoQ10) and glutathione, and antioxidant enzymes such as superoxide dismutase (SOD), catalase, and glutathione peroxidase;

(xxxii) anti-inflammatory agents including, e.g., methyl salicylate, aspirin, ibuprofen, and naproxen. Additional anti-inflammatories useful in topical applications include corticosteroids, such as, but not limited to, flurandrenolide, clobetasol propionate, halobetasol propionate, fluticasone propionate, betamethasone dipropionate, betamethasone benzoate, betamethasone valerate, desoximethasone, dexamethasone, diflorasone diacetate, mometasone furoate, amcinodine, halcinonide, fluocinonide, fluocinolone acetonide, desonide, triamcinolone acetonide, hydrocortisone, hydrocortisone acetate, fluoromethalone, methylprednisolone, and predinicarbate;

(xxxiii) anesthetics that can be delivered locally including benzocaine, butamben, butamben picrate, cocaine, procaine, tetracaine, lidocaine and pramoxine hydrochloride;

(xxxiv) analgesics such as ibuprofen, diclofenac, capsaicin, and lidocaine;

(xxxv) antifungal agents. Non-limiting examples are micanazole, clotrimazole, butoconazole, fenticonasole, tioconazole, terconazole, sulconazole, fluconazole, haloprogin, ketonazole, ketoconazole, oxinazole, econazole, itraconazole, torbinafine, nystatin and griseofulvin;

(xxxvi) antibiotics such as erythromycin, clindamycin, synthomycin, tetracycline, metronidazole and the like;

(xxxvii) anti-viral agents including famcyclovir, valacyclovir and acyclovir;

(xxxviii) anti-parasitic agents such as scabicedes, such as permethrin, crotamiton, lindane and ivermectin;

(xil) anti-infectious and anti-acne agents including benzoyl peroxide, sulfur, resorcinol and salicylic acid;

(xl) dermatological active ingredients useful in topical applications including, e.g., jojoba oil and aromatic oils such as methyl salicylate, wintergreen, peppermint oil, bay oil, *eucalyptus* oil and citrus oils, as well as ammonium phenolsulfonate, bismuth subgallate, zinc phenolsulfonate and zinc salicylate;

(xli) enzymes and co-enzymes useful for topical application including co-enzyme Q10, papain enzyme, lipases, proteases, superoxide dismutase, fibrinolysin, desoxyribonuclease, trypsin, collagenase and sutilains;

(xlii) skin whitening agents such as hydroquinone and monobenzone;

(xliii) anti-histamines including chlorpheniramine, brompheniramine, dexchlorpheniramine, tripolidine, clemastine, diphenhydramine, prometazine, piperazines, piperidines, astemizole, loratadine and terfonadine;

(xliv) chemotherapeutic agents such as 5-fluorouracil, masoprocol, mechlorethamine, cyclophosphamide, vincristine, chlorambucil, streptozocin, methotrexate, bleomycin, dactinomycin, daunorubicin, coxorubicin and tamoxifen; and (xlv) insect repellents including pediculicides for treatment of lice, such as pyrethrins, permethrin, malathion, lindane and the like.

In addition to the active materials listed above, the products of this invention can also contain, for example, the following dyes, colorants or pigments: lactoflavin (riboflavin), beta-carotene, riboflavin-5'-phosphate, alpha-carotene, gamma-carotene, cantaxanthin, erythrosine, curcumin, quinoline yellow, yellow orange S, tartrazine, bixin, norbixin (annatto, orlean), capsanthin, capsorubin, lycopene, beta-apo-8'-carotenal, beta-apo-8'-carotenic acid ethyl ester, xantophylls (flavoxanthin, lutein, cryptoxanthin, rubixanthin, violaxanthin, rodoxanthin), fast carmine (carminic acid, cochineal), azorubin, cochineal red A (Ponceau 4 R), beetroot red, betanin, anthocyanins, amaranth, patent blue V, indigotine I (indigo-carmine), chlorophylls, copper compounds of chlorophylls, acid brilliant green BS (lissamine green), brilliant black BN, vegetable carbon, titanium dioxide, iron oxides and hydroxides, calcium carbonate, aluminum, silver, gold, pigment rubine BK (lithol rubine BK), methyl violet B, victoria blue R, victoria blue B, acilan brilliant blue FFR (brilliant wool blue FFR), naphthol green B, acilan fast green 10 G (alkali fast green 10 G), ceres yellow GRN, sudan blue II, ultramarine, phthalocyanine blue, phthalocayanine green, fast acid violet R. Further naturally obtained extracts (for example paprika extract, black carrot extract, red cabbage extract) can be used for coloring purposes. Goods results are also achieved with the colors named in the following, the so-called aluminum lakes: FD & C Yellow 5 Lake, FD & C Blue 2 Lake, FD & C Blue 1 Lake, Tartrazine Lake, Quinoline Yellow Lake, FD & C Yellow 6 Lake, FD & C Red 40 Lake, Sunset Yellow Lake, Carmoisine Lake, Amaranth Lake, Ponceau 4R Lake, Erythrosyne Lake, Red 2G Lake, Allura Red Lake, Patent Blue V Lake, Indigo Carmine Lake, Brilliant Blue Lake, Brown HT Lake, Black PN Lake, Green S Lake and mixtures thereof.

Additional fragrance ingredients are described in, e.g., Arctander (2000) *Perfume Flavors and Chemicals*. Vols. I and II, Montclair, N.J.; *The Merck Index*, 8$^{th}$ Edition (1968) Merck & Co., Inc. Rahway, N.J.; *Allured's Flavor and Fragrance Materials* (2015) Allured Publishing Corp.

The fragrance accord can further contain one or more antibacterials at a level of 0.05 to 5 wt % (0.05 to 2 wt %, 0.1 to 0.5 wt %). Examples of the antibacterial include methyl cresol, linalool, pine super extreme, bisguanidines (e.g., chlorhexidine digluconate), diphenyl compounds, benzyl alcohols, trihalocarbanilides, quaternary ammonium compounds, ethoxylated phenols, and phenolic compounds, such as halo-substituted phenolic compounds, like PCMX (i.e., p-chloro-m-xylenol), triclosan (i.e., 2,4,4'-trichloro-2' hydroxy-diphenylether), thymol, and triclocarban.

The fragrance accord can also contain 0.05 to 20 wt % (0.1 to 15 wt %, 0.2 to 10 wt %, and 0.3 to 5 wt %) one or more malodor counteracting agents including an α,β-unsaturated carbonyl compounds including but not limited to those disclosed in U.S. Pat. No. 6,610,648 and EP 2,524,704, amyl cinnamaldehyde, benzophenone, benzyl benzoate, benzyl isoeugenol, benzyl phenyl acetate, benzyl salicylate, butyl cinnamate, cinnamyl butyrate, cinnamyl isovalerate, cinnamyl propionate, decyl acetate, ethyl myristate, isobutyl cinnamate, isoamyl salicylate, phenethyl benzoate, phenethyl phenyl acetate, triethyl citrate, tripropylene glycol n-butyl ether, isomers of bicyclo[2.2.1]hept-5-ene-2-carboxylic acid, ethyl ester, nano silver, zinc undecenylate, β-naphthyl methyl ether, β-naphthyl ketone, benzyl acetone. They may include mixture of hexahydro-4,7-methanoinden-5-yl propionate and hexahydro-4,7-methanoinden-6-yl propionate; 4-(2,6,6-trimethyl-2-cyclohexen-1-yl)-3-methyl-3-buten-2-one; 3,7-dimethyl-2,6-nonadien-1-nitrile; dodecahydro-3a,6,6,9a-tetramethylnaphtho(2,1-b)furan; ethylene glycol cyclic ester of n-dodecanedioic acid; 1-cyclohexadecen-6-one; 1-cycloheptadecen-10-one; and corn mint oil. They may also include 1-cyclohexylethan-1-yl butyrate; 1-cyclohexylethan-1-yl acetate; 1-cyclohexylethan-1-ol; 1-(4'-methylethyl)cyclohexylethan-1-yl propionate; and 2'-hydroxy-1'-ethyl(2-phenoxy)acetate each of which compound is marketed under the trademark VEILEX by International Flavors & Fragrances Inc. More suitable malodor counteracting agents are polymers containing an a-keto, benzaldehyde, or α,β-unsaturated carbonyl moiety, such as those described in US Application Publications 2012/0294821, 2013/0101544 and 2013/0101545.

The present fragrance accord defines a set of fragrance ingredients which, contrary to conventional physical-chemistry knowledge, perfumery expertise and normal practice, are detected faster by the human nose, have enhanced initial bloom and bloom/room filing sensory performance. The present fragrance accord of this invention also shows benefits such as improved malodor coverage, hygiene, antibacterial, fresh and/or clean attributes. Given the higher level of performance attained with the fragrance accord, lower amounts of fragrance (e.g., 10-30% of conventional fragrances) can be dosed into product formulations thereby reducing the environmental load as well as allergenic issues. In addition, many of the Class 1 fragrance ingredients are available from natural renewable resources (e.g., from fermentation processes or by simple extraction of plant material).

The high intensity bloom fragrance accord of this invention can be used as is (i.e., neat) or dosed from 0.1% to 25% in a fragrance formula to generate a full formula system. Advantageously, both the fragrance accord alone and full formula system are capable of having a speed of diffusivity, an odor performance, and/or a bloom/room filling intensity at parity or higher than the formulas best in class using the same or lower dosage level.

Alternatively, the high intensity bloom fragrance accord of this invention can be encapsulated in a delivery system. A wide variety of encapsulating materials exist which allow for delivery of fragrances at various times in the cleaning or conditioning process. Suitable encapsulating materials a include starches, oligosaccharides, cyclodextrins, polyethylenes, polyamides, polystyrenes, polyisoprenes, polycarbonates, polyesters, polyacrylates, vinyl polymers polyurethanes, amorphous silica, precipitated silica, fumed silica, aluminosilicates, such as zeolites and alumina, and mixtures thereof. In the event that the encapsulating material includes amorphous silica, precipitated silica, fumed silica or aluminosilicates such as zeolite and alumina, the pore volume is at least 0.1 ml/g and includes pores with a diameter between 0.4-10 nm. Suitable delivery systems include those described in WO 2015/023961, WO 2014/011860, U.S. Pat. No. 7,196,049, US 2007/0138674, US 2014/0044760, US 2014/0044761, US 2014/0287008, and US 2013/0330292.

A particular aspect of the present invention is to provide high intensity, consumer acceptable fragrances, suitable for use in consumer products including liquid detergents, powder detergent, bar soap, etc. As secondary benefits, the fragrance accord provides enhanced malodor coverage, superior hygiene, fresh and clean consumer attributes, and/or potentially less environmental and allergenic impacts due to the possibility of using a lower dosage of the invention. Accordingly, the invention also provides a fabric care product containing an effective amount of the high intensity bloom fragrance accord of disclosed herein and an unfragranced fabric care product base. In some embodiments, the high intensity bloom fragrance accord provides enhanced bloom intensity for speed of diffusivity, and bloom/room filling; increased malodor coverage/reduction; fresh and clean fragrance sensory attributes and/or hygiene/antibacterial properties.

The consumer product can contain any fragrance accord described above at a level of 0.01 to 20 wt % (e.g., 0.02 to 10 wt %, 0.05 to 5 wt %, 0.05 to 2 wt %, 0.1 to 0.5 wt %), wherein the lower limit may be 0.01, 0.02, 0.05, 0.1, 0.2, or 0.5 wt %, and the upper limit may be 20, 15, 10, 8, 6, 5, 3, 2, 1, 0.8, or 0.5 wt %.

A fabric care product of the invention is intended to include powder detergent product, liquid detergent product, or fabric conditioner product. For example, powder laundry detergents (machine and handwashing) are described in U.S. Pat. Nos. 5,840,668, 5,227,084, 6,080,711, 5,443,751 and 5,500,153. liquid laundry detergents include those systems described in U.S. Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818. Fabric softener and conditioner products are described, e.g., U.S. Pat. Nos. 5,652,206, 6,949,500, 6,593,289, 4,446,032 and 9,150,819.

Applications.

The fragrance accord of this invention, either as a neat oil or encapsulated in a delivery system, is well-suited for use, without limitation, in the following products:

a) Household products
  i. Liquid or Powder Laundry Detergents which can use the present invention include those systems described in U.S. Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818.
  ii. Unit Dose Pouches, Tablets and Capsules such as those described in EP 1 431 382 A1, US 2013/0219996 A1, US 2013/0284637 A1, and U.S. Pat. No. 6,492,315. These unit dose formulations can contain high concentrations of a functional material (e.g., 5-100% fabric softening agent or detergent active), fragrance (e.g., 0.5-100%, 0.5-40%, and 0.5-15%), and flavor (e.g., 0.1-100%, 0.1-40%, and 1-20%). They can contain no water to limit the water content as low as less than 30% (e.g., less than 20%, less than 10%, and less than 5%).
  iii. Scent Boosters such as those described in U.S. Pat. Nos. 7,867,968, 7,871,976, 8,333,289, US 2007/0269651 A1, and US2014/0107010 A1.
  iv. Fabric Care Products such as Rinse Conditioners (containing 1 to 30 weight % of a fabric conditioning active), Fabric Liquid Conditioners (containing 1 to 30 weight % of a fabric conditioning active), Tumble Drier Sheets, Fabric Refreshers, Fabric Refresher Sprays, Ironing Liquids, and Fabric Softener Systems such as those described in U.S. Pat. Nos. 6,335,315, 5,674,832, 5,759,990, 5,877,145, 5,574,179, 5,562,849, 5,545,350, 5,545,340, 5,411,671, 5,403,499, 5,288,417, 4,767,547 and 4,424,134. Liquid fabric softeners/fresheners contains at least one fabric softening agent present, preferably at a concentration of 1 to 30% (e.g., 4 to 20%, 4 to 10%, and 8 to 15%). The ratio between the active material and the fabric softening agent can be 1:500 to 1:2 (e.g., 1:250 to 1:4 and 1:100 to 1:8). As an illustration, when the fabric softening agent is 5% by weight of the fabric softener, the active material is 0.01 to 2.5%, preferably 0.02 to 1.25% and more preferably 0.1 to 0.63%. As another example, when the fabric softening agent is 20% by weight of the fabric softener, the active material is 0.04 to 10%, preferably 0.08 to 5% and more preferably 0.4 to 2.5%. The active material is a fragrance, malodor counteractant or mixture thereof. The liquid fabric softener can have 0.15 to 15% of capsules (e.g., 0.5 to 10%, 0.7 to 5%, and 1 to 3%). When including capsules at these levels, the neat oil equivalent (NOE) in the softener is 0.05 to 5% (e.g., 0.15 to 3.2%, 0.25 to 2%, and 0.3 to 1%).
    Suitable fabric softening agents include cationic surfactants. Non-limiting examples are quaternary ammonium compounds such as alkylated quaternary ammonium compounds, ring or cyclic quaternary ammonium compounds, aromatic quaternary ammonium compounds, diquaternary ammonium compounds, alkoxylated quaternary ammonium compounds, amidoamine quaternary ammonium compounds, ester quaternary ammonium compounds, and mixtures thereof. Fabric softening compositions, and components thereof, are generally described in US 2004/0204337 and US 2003/0060390. Suitable softening agents include esterquats such as Rewoquat WE 18 commercially available from Evonik Industries and Stepantex SP-90 commercially available from Stepan Company.
  v. Liquid dish detergents such as those described in U.S. Pat. Nos. 6,069,122 and 5,990,065
  vi. Automatic Dish Detergents such as those described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562
  vii. All-purpose Cleaners including bucket dilutable cleaners and toilet cleaners
  viii. Bathroom Cleaners
  ix. Bath Tissue
  x. Rug Deodorizers
  xi. Candles
  xii. Room Deodorizers
  xiii. Floor Cleaners
  xiv. Disinfectants
  xv. Window Cleaners
  xvi. Garbage bags/trash can liners
  xvii. Air Fresheners including room deodorizer and car deodorizer, scented candles, sprays, scented oil air freshener, Automatic spray air freshener, and neutralizing gel beads
  xviii. Moisture absorber
  xix. Household Devices such as paper towels and disposable Wipes
  xx. Moth balls/traps/cakes
b) Baby Care Products
  i. Diaper Rash Cream/Balm
  ii. Baby Powder
c) Baby Care Devices
  i. Diapers
  ii. Bibs
  iii. Wipes
d) Oral Care Products. Tooth care products (as an example of preparations according to the invention used for oral care) generally include an abrasive system (abrasive or polishing agent), for example silicic acids, calcium carbonates, calcium phosphates, aluminum oxides and/or hydroxylapatites, surface-active substances, for example sodium lauryl sulfate, sodium lauryl sarcosinate and/or cocamidopropylbetaine, humectants, for example glycerol and/or sorbitol, thickening agents, for example carboxymethyl cellulose, polyethylene glycols, carrageenan and/or Laponite™, sweeteners, for example saccharin, taste correctors for unpleasant taste sensations, taste correctors for further, normally not unpleasant taste sensations, taste-modulating substances (for example inositol phosphate, nucleotides such as guanosine monophosphate, adenosine monophosphate or other substances such as sodium glutamate or 2-phenoxypropionic acid), cooling active ingredients, for example menthol derivatives, (for example L-menthyllactate, L-menthylalkylcarbonates, menthone ketals, menthane carboxylic acid amides), 2,2,2-trialkylacetic acid amides (for example 2,2-diisopropylpropionic acid methyl amide), icilin and icilin derivatives, stabilizers and active ingredients, for example sodium fluoride, sodium monofluorophosphate, tin difluoride, quaternary ammonium fluorides, zinc citrate, zinc sulfate, tin pyrophosphate, tin dichloride, mixtures of various pyrophosphates, triclosan, cetylpyridinium chloride, aluminum lactate, potassium citrate, potassium nitrate, potassium chloride, strontium chloride, hydrogen peroxide, flavorings and/or sodium bicarbonate or taste correctors.

i. Tooth Paste. An exemplary formulation as follows:
    1. calcium phosphate 40-55%
    2. carboxymethyl cellulose 0.8-1.2%
    3. sodium lauryl sulfate 1.5-2.5%
    4. glycerol 20-30%
    5. saccharin 0.1-0.3%
    6. flavor oil 1-2.5%
    7. water q.s. to 100%
      A typical procedure for preparing the formulation includes the steps of (i) mixing by a blender according to the foregoing formulation to provide a toothpaste, and (ii) adding a composition of this invention and blending the resultant mixture till homogeneous.
  ii. Tooth Powder
  iii. Oral Rinse
  iv. Tooth Whiteners
  v. Denture Adhesive e) Health Care Devices
  i. Dental Floss
  ii. Toothbrushes
  iii. Respirators
  iv. Scented/flavored condoms f) Feminine Hygiene Products such as Tampons, Feminine Napkins and Wipes, and Pantiliners g) Personal Care Products: Cosmetic or pharmaceutical preparations, e.g., a "water-in-oil" (W/0) type emulsion, an "oil-in-water" (0/W) type emulsion or as multiple emulsions, for example of the water-in-oil-in-water (W/O/W) type, as a PIT emulsion, a Pickering emulsion, a micro-emulsion or nano-emulsion; and emulsions which are particularly preferred are of the "oil-in-water" (0/W) type or water-in-oil-in-water (W/O/W) type. More specifically,
  i. Personal Cleansers (bar soaps, body washes, and shower gels)
  ii. In-shower conditioner
  iii. Sunscreen ant tattoo color protection (sprays, lotions, and sticks)
  iv. Insect repellants
  v. Hand Sanitizer
  vi. Antiinflammatory balms, ointments, and sprays
  vii. Antibacterial ointments and creams
  viii. Sensates
  ix. Deodorants and Antiperspirants including aerosol and pump spray antiperspirant, stick antiperspirant, roll-on antiperspirant, emulsion spray antiperspirant, clear emulsion stick antiperspirant, soft solid antiperspirant, emulsion roll-on antiperspirant, clear emulsion stick antiperspirant, opaque emulsion stick antiperspirant, clear gel antiperspirant, clear stick deodorant, gel deodorant, spray deodorant, roll-on, and cream deodorant.
  x. Wax-based Deodorant. An exemplary formulation as follows:
    1. Parafin Wax 10-20%
    2. Hydrocarbon Wax 5-10%
    3. White Petrolatum 10-15%
    4. Acetylated Lanolin Alcohol 2-4%
    5. Diisopropyl Adipate 4-8%
    6. Mineral Oil 40-60%
    7. Preservative (as needed)
      The formulation is prepared by (i) mixing the above ingredients, (ii) heating the resultant composition to 75° C. until melted, (iii) with stirring, adding 4% cryogenically ground polymer containing a fragrance while maintaining the temperature 75° C., and (iv) stirring the resulting mixture in order to ensure a uniform suspension while a composition of this invention is added to the formulation.
  xi. Glycol/Soap Type Deodorant. An exemplary formulation as follows:
    1. Propylene Glycol 60-70%
    2. Sodium Stearate 5-10%
    3. Distilled Water 20-30%
    4. 2,4,4-Trichloro-2'-Hydroxy Diphenyl Ether, manufactured by the Ciba-Geigy Chemical Company and a Trademark of the Ciba-Geigy Chemical Company) 0.01-0.5%
      The ingredients are combined and heated to 75° C. with stirring until the sodium stearate has dissolved. The resulting mixture is cooled to 40° C. followed by addition of a composition of this invention.
  xii. Lotion including body lotion, facial lotion, and hand lotion
  xiii. Body powder and foot powder
  xiv. Toiletries
  xv. Body Spray
  xvi. Shave cream and male grooming products
  xvii. Bath Soak
  xviii. Exfoliating Scrub h) Personal Care Devices
  i. Facial Tissues
  ii. Cleansing wipes i) Hair Care Products
  i. Shampoos (liquid and dry powder)
  ii. Hair Conditioners (Rinse-out conditioners, leave-in conditioners, and cleansing conditioners)
  iii. Hair Rinses
  iv. Hair Refreshers
  v. Hair perfumes
  vi. Hair straightening products
  vii. Hair styling products, Hair Fixative and styling aids
  viii. Hair combing creams ix. Hair wax
x. Hair foam, hair gel, nonaerosol pump spray
xi. Hair Bleaches, Dyes and Colorants
xii. Perming agents
xiii. Hair wipes j) Beauty Care
i. Fine Fragrance—Alcoholic. Compositions and methods for incorporating fragrance capsules into alcoholic fine fragrances are described in U.S. Pat. No. 4,428,869. Alcoholic fine fragrances may contain the following:
  1. Ethanol (1-99%)
  2. Water (0-99%)
  3. A suspending aide including but not limited to: hydroxypropyl cellulose, ethyl cellulose, silica, microcrystalline cellulose, carrageenan, propylene glycol alginate, methyl cellulose, sodium carboxymethyl cellulose or xanthan gum (0.1-1%)
  4. Optionally an emulsifier or an emollient may be included including but not limited to those listed above
ii. Solid Perfume
iii. Lipstick/lip balm
iv. Make-up cleanser
v. Skin care cosmetic such as foundation, pack, sunscreen, skin lotion, milky lotion, skin cream, emollients, skin whitening
vi. Make-up cosmetic including manicure, mascara, eyeliner, eye shadow, liquid foundation, powder foundation, lipstick and cheek rouge k) Consumer goods packaging such as fragranced cartons, fragranced plastic bottles/boxes l) Pet care products
i. Cat litter
ii. Flea and tick treatment products
iii. Pet grooming products
iv. Pet shampoos
v. Pet toys, treats, and chewables
vi. Pet training pads
vii. Pet carriers and crates All parts, percentages and proportions refer to herein and in the claims are by weight unless otherwise indicated.

The values and dimensions disclosed herein are not to be understood as being strictly limited to the exact numerical values recited. Instead, unless otherwise specified, each such value is intended to mean both the recited value and a functionally equivalent range surrounding that value. For example, a value disclosed as "50%" is intended to mean "about 50%."

Mixtures of fragrance ingredients are known by those skilled in the art of fragrances and perfumes as "accords." The term "accord" as used herein is defined as "a mixture of two or more 'fragrance ingredients' which are artfully combined to impart a pleasurable scent, odor, essence, or fragrance characteristic."

The terms fragrance ingredient or composition as used herein are deemed to define a variety of fragrance materials of both natural and synthetic origin. For the purposes of the present invention "fragrance ingredients" are herein defined as compounds having a molecular weight of at least 100 g/mol and which are useful in imparting an odor, fragrance, essence, or scent either alone or in combination with other "fragrance ingredients." They include single compounds and mixtures that are volatile and odorous, in liquid or solid form, hydrophilic or hydrophobic. Specific examples may be found in the current literature, e.g. in Perfume and Flavor Chemicals by S. Arctander, Montclair N.J. (USA); Fenaroli's Handbook of flavour Ingredients, CRC Press or Synthetic Food Adjuncts by M.B. Jacobs, van Nostrand Co., Inc.; Steffen Arctander Allured Pub. Co. (1994) and "Perfumes: Art, Science and Technology"; and Muller, P. M. and Lamparsky, D., Blackie Academic and Professional (1994).

The terms "g," "mg," and "μg" refer to "gram," "milligram," and "microgram," respectively. The terms "L" and "mL" refer to "liter" and "milliliter," respectively. The term "cm" refers to "centimeter." The terms "cm/second" and "cm/s" both refer to "centimeter/second."

The invention is described in greater detail by the following non-limiting examples. Without further elaboration, it is believed that one skilled in the art can, based on the description herein, utilize the present invention to its fullest extent. All publications cited herein are incorporated by reference in their entirety.

Examples 1-3

Tests were conducted using a typical fragrance probe as a comparative fragrance accord. The probe included 0.7 wt % Class 1 fragrance ingredients (i.e., diphenyl oxide, rose oxide, manzanate, and galbascone), 20.7 wt % Class 2 fragrance ingredients (i.e.,oxydibenzene, (2R,4S)-4-methyl-2-(2-methylprop-1-en-1-yl)tetrahydro-2H-pyran, ethyl 2-methylpentanoate, and 1-(5,5-dimethylcyclohex-1-en-1-yl)pent-4-en-1-one), 20.7 wt % Class 2 fragrance ingredients (i.e., 2-methoxynaphthalene, 3a,4,5,6,7,7a-hexahydro-1H-4,7-methanoinden-5-yl propionate, (E)-3-methyl-4-(2,6,6-trimethylcyclohex-2-en-1-yl)but-3-en-2-one, 4-methoxybenzaldehyde, dodecanal, (E)-4-methyldec-3-en-5-ol, and (1S,2R)-2,4-dimethylcyclohex-3-ene-1-carbaldehyde), 78.4% class 3 fragrance ingredients, and 0.2 wt % essential oil.

Three fragrance accords of this invention (Accords A, B and C) were created following the specifications defined herein.

Accord A contains 9% Class 1 fragrance ingredients (i.e., 1-(5,5-dimethylcyclohex-1-en-1-yl)pent-4-en-1-one, oxydibenzene, methyl benzoate, 1,3,3-trimethyl-2-oxabicyclo[2.2.2]octane, ethyl 2-methylbutanoate, methyl 2-aminobenzoate), 13.95% Class 2 fragrance ingredients (i.e., 2-methoxynaphthalene, (E)-tridec-2-enenitrile, 3a,4,5,6,7,7a-hexahydro-1H-4,7-methanoinden-5-yl propionate, (E)-4-(2,6,6-trimethylcyclohex-1-en-1-yl)but-3-en-2-one, (E)-3-methyl-4-(2,6,6-trimethylcyclohex-2-en-1-yl)but-3-en-2-one, 4-methoxybenzaldehyde, dodecanal, (E)-4-methyldec-3-en-5-ol, (1R,2R,4R)-1,7,7-trimethylbicyclo[2.2.1]heptan-2-ol, (E)-1-methoxy-4-(prop-1-en-1-yl)benzene, 3,7-dimethyloct-6-enenitrile, (1S,2R)-2,4-dimethylcyclohex-3-ene-1-carbaldehyde, pine super xtreme), 70.55% Class 3 fragrance ingredients such as 4,7-methano-1H-indenol, 3a,4,5,6,7,7a-hexahydro-, acetate, 1-2,6,6-trimethyl-3-cyclohexen-1-yl-2-buten-1-one, and 6.50% essential oil (i.e. basil oil, violet leaf abs, grapefruit oil).

Accord B contains 13.65% Class 1 fragrance ingredients (i.e., methyl 2-aminobenzoate, 1-(5,5-dimethylcyclohex-1-en-1-yl)pent-4-en-1-one, 4-methylene-2-phenyltetrahydro-2H-pyran, oxydibenzene, methyl benzoate, (2R,4S)-4-methyl-2-(2-methylprop-1-en-1-yl)tetrahydro-2H-pyran, (2-methoxyethyl)benzene, dipentene, 1,3,3-trimethyl-2-oxabicyclo[2.2.2]octane, (1R,2R,4R)-ethyl bicyclo[2.2.1]hept-5-ene-2-carboxylate, 2-isobutyl-3-methoxypyrazine, 1-methoxy-4-methylbenzene, (3aR,8b S)-2,2,6,6,7,8,8-heptamethyldecahydro-2H-indeno[4,5-b]furan), 61.40% Class 2 fragrance ingredients (i.e., 2-methoxynaphthalene, tridecene-2-nitrile, 3a,4,5,6,7,7a-hexahydro-1H-4,7-methanoinden-5-yl propionate, (E)-4-(2,6,6-trimethylcyclohex-1-en-1-yl)but-3-en-2-one, (E)-3-methyl-4-(2,6,6-trimethylcyclohex-2-en-1-yl)but-3-en-2-one, 4-methoxybenzaldehyde, dodecanal, 3-methyl-2-pentylcyclopent-2-en-1-one, (1R,2R,4R)-1,7,7-trimethylbicyclo[2.2.1]heptan-2-ol, (E)-undec-9-enal, (E)-1-methoxy-4-(prop-1-en-1-yl)benzene, 3,7-dimethyloct-6-enenitrile, 3,7-dimethylocta-1,6-dien-3-ol, (1 S,2R)-2,4-dimethylcyclohex-3-ene-1-carbaldehyde, octanal, pine super xtreme), 13.21% Class 3 fragrance ingredients such as trisamber and ald c-12 MNA, and 11.74% essential oil (i.e., basil oil, clove leaf oil, petitgrain oil).

Accord C contains 71.58% Class 1 fragrance ingredients (i.e., 1-(5,5-dimethylcyclohex-1-en-1-yl)pent-4-en-1-one, 4-methylene-2-phenyltetrahydro-2H-pyran, oxydibenzene, 1,3,3-trimethyl-2-oxabicyclo[2.2.2]octane, ethyl hexanoate, ethyl 2-methylbutanoate, (1R,2R,4R)-ethyl bicyclo[2.2.1]hept-5-ene-2-carboxylate, thiazole (2-isopropyl 4-methyl), 2-isobutyl-3-methoxypyrazine), 25.46% class 2 fragrance ingredients (i.e., (E)-4-(2,6,6-trimethylcyclohex-2-en-1-yl)but-3-en-2-one, 2-methoxynaphthalene, 3a,4,5,6,7,7a-hexahydro-1H-4,7-methanoinden-5-yl propionate, (E)-4-(2,6,6-trimethylcyclohex-1-en-1-yl)but-3-en-2-one, dodecanal, (E)-4-methyldec-3-en-5-ol, 3,7-dimethyloct-6-enenitrile, 3-(4-methylcyclohex-3-en-1-yl)butanal, 3,7-dimethylocta-1,6-dien-3-ol, (1 S,2S)-2-(tert-butyl)cyclohexan-1-ol, 2,6-dimethylhept-5-enal, (1 S,2R)-2,4-dimethylcyclohex-3-ene-1-carbaldehyde, octanal, 1-methyl-4-(propan-2-ylidene)cyclohex-1-ene, pine super extreme), 0.06% Class 3 fragrance ingredients and 2.9% essential oil (i.e., sinensal oil and violet leaf abs).

A standard fragrance probe was used as a comparison and also as a base for diluting Accords A, B, and C. A commercially available fragrance product, i.e., a starch encapsulated fragrance benchmark, was used as comparison.

Each of Fragrance Accords A, B, and C was dosed at 25% in the standard fragrance probe to produce Full Formula System A, B, and C (i.e., 25% fragrance accord A, B, or C+75% standard fragrance probe). Each of the three full formulae systems was dosed at 0.3% and 0.2% in an unfragranced powder detergent base. A panel of six judges evaluated the speed of diffusivity, fragrance intensity of the fragranced powder detergent (i.e., fragrance accord+fragrance probe+unfragranced powder base). Further, the fragrance accords (dosed at 0.1%) were compared to the starch encapsulated fragrance benchmark and the standard fragrance probe (neat oil). The three full formula systems were screened via the trained sensory panel for speed of diffusivity and for fragrance intensity. In the fragrance intensity screening, each fragrance accord was scored in a Labeled Magnitude Scale (LMS) of 0 to 100. A score of 5 indicates that the fragrance accord has a weak smell, a score of 17 indicates a moderate smell, and a score of above 35 indicates a very strong smell. The full formula systems were compared to a total product formulation benchmark, which contains neat oil (0.2%) plus the starch encapsulated fragrance benchmark (0.05% NOE), and also against the standard fragrance probe (neat oil at 0.1%). All statistical results presented were evaluated through ANOVA considering a 95% level of confidence.

Speed of Diffusivity.

The results of this analysis on aged samples (e.g., for 2 weeks) showed that all three fragrance accords had enhanced performance for speed of diffusivity when compared with the reference fragrance probe and the fragrance starch probe. Moreover, unexpectedly, the three fragrance accords showed significantly better speed of diffusivity than the benchmark product. Accords A, B, and C, respectively, had a fragrance intensity of 29.13, 22.91, and 28.39. By contrast, the standard fragrance probe had a fragrance intensity of 16.17 and the starch encapsulated fragrance benchmark had a fragrance intensity of 18.45. As to the speed of diffusivity, Accords A, B, and C, respectively, had a speed of diffusivity of 3.79 seconds, 4.44 seconds, and 4.18 seconds. As a comparison, the standard fragrance probe and the starch encapsulated fragrance benchmark had a speed of diffusivity of 4.74 seconds and 5.74 seconds, respectively.

In terms of the three full fragrance systems, parity levels in terms were observed for speed of diffusivity (one full fragrance system has faster speed of diffusivity also) when compared with the fragrance probe and the benchmark product.

Fragrance Intensity.

Results showed that all three fragrance accords had significantly higher fragrance strength than the reference fragrance probe.

Furthermore, it was observed that all three Full Fragrance Systems A, B, and C had significantly higher fragrance strength than the standard fragrance probe and were parity versus the benchmark product containing a fragrance neat oil and a starch encapsulated fragrance.

Dosed at 0.3% in the powder detergent base, Full Fragrance Systems A, B, and C, respectively, had a fragrance intensity of 18.78, 16.95, and 18.79, and a speed of diffusivity of 4.47, 4.09, and 4.56 seconds. The benchmark product had a fragrance intensity of 18.45 and a speed of diffusivity of 5.74.

Dosed at 0.2% in the powder detergent base, Full Fragrance Systems A, B, and C, respectively, had a fragrance intensity of 16.07, 15.06, and 16.43.

This result was unexpected because the benchmark contained fragrance neat oil plus an encapsulation technology (starch), which is known in the art for providing a significant improvement in fragrance performance at the soaking/bloom stage when in contact with the water phase (for aged samples due to chemical protection of fragrance ingredients against consumer product base). Further, it was observed that any of the full fragrance systems containing the blooming fragrance accord as neat oil had fragrance performance intensities that were parity with a benchmark product which is a full fragrance system (containing a neat oil plus and an encapsulation technology).

Analytical headspace measurement. The headspace of the fragrance probe+accord (accord 25%, probe 75%, total dosage at 0.1%) was measured through standardized analytical dynamic headspace methods and revealed a significantly higher amount of headspace molecules than the probe alone (dosed at 0.1%) both at short and long times after dissolution of the fragranced powder detergent in water. Moreover, odor intensities were calculated from measured peak areas using the odor value concept (OV). Details about the OV model and its applicability to fragrance formulations and sensory perception can be found in the literature. See M. Teixeira et al., Perfume Engineering: Design, Performance & Classification, BH Elsevier, Oxford, U K, 2013. Though this approach it was also observed that the calculated intensity of the odor of the fragrance probe+accord was significantly higher than from the probe alone, thus validating the analytical measurement. This shows the benefit in terms of enhanced fragrance performance of the accords disclosed here.

Malodor Coverage.

The fragrance accords were also designed using the malodor coverage/antimicrobial property database. In this respect, specific fragrance materials with malodor coverage and antimicrobial properties were included in the formulation (e.g., pine super extreme, 3,7-dimethylocta-1,6-dien-3-ol, 3,7-dimethyloctan-3-ol, and 3-ethoxy-4-hydroxybenzaldehyde, among others). For example, it has been found that perfume compositions containing ≥0.05% of at least one of the antibacterial/perfume compositions disclosed in U.S. Pat. No. 6,495,512 can be used to impart interesting herbaceous, citrusy, spicy, floral, sweet and vanillin aromas with earthy, musty and green undertones while having antibacterial properties. The results of this analysis showed that the two fragrance accords containing malodor counteractive agents had significant enhancement in malodor coverage levels for mildew and sweat versus the citrus oil benchmark.

Hygiene/antibacterial.

The fragrance accords can contain antibacterial ingredients described above. See U.S. Pat. No. 6,495,512 for a list of suitable antibacterial ingredients. It has been found that fragrance accords of this invention containing ≥0.05% of at least one antibacterial can be used to impart appealing aromas while having anti-bacterial properties. Fragrance ingredients with high antibacterial activity against *E. coli, E. hirae, S. aureos* and other bacteria include 1-methoxy-4-methylbenzene, 3,7-dimethylocta-1,6-dien-3-ol, and pine super extreme, among others.

Examples 4 and 5

Accord D of this invention was prepared by using (i) 8.1% of four Class 1 ingredients: rose oxide, galbascone, tropicalia, and ethyl-2-methyl butyrate.

Fragrance 1 of this invention was prepared by adding 5 parts of Accord D to 75 parts of fragrance Serena (Commercially available from International Flavors & Fragrances, Union Beach, N.J.). Fragrance Serena contained only 0.375% of Class 1 ingredients and was used as a control.

Shampoo Composition 1 of this invention was prepared by dosing Fragrance 1 in an unfragranced model shampoo base at a level of 1%. The shampoo composition was macerated for at least 24 hours at room temperature before evaluation.

A comparative shampoo composition was prepared by mixing fragrance Serena with the unscented shampoo base at the same dosage as Shampoo Composition 1.

Shampoo Performance

Shampoo Composition 1 and the comparative shampoo composition each were applied to wet hair swatches with excess water squeezed out. The hair swatches were then lathered and rinsed with water.

A trained panel of judges evaluated the fragrance intensity on a scale ranging from 0 to 100. A numerical value of 5 indicated the hair swatches produced a weak intensity, while a value of 30 indicated the hair swatches generated a very strong smell.

Unexpectedly, the hair swatches treated with Shampoo Composition 1 had a fragrance intensity of 13.6 at the bloom stage while the hair swatches treated with the comparative shampoo composition had a fragrance intensity of 12.6.

Examples 6-8

Three fragrance accords of this invention, i.e., Accords E, F, and G, were prepared.
Accord E contained 9% of Class 1 ingredients.
Accord F contained 11% of Class 1 ingredients.
Accord G contained 13% of Class 1 ingredients.

Accords E, F and G contained the same fragrance ingredients except that the amount of Class 1 Ingredients was different. See Table 3 below.

Comparative Accord 2' was prepared using the same fragrance ingredients as Accord E but with only 5% of Class 1 ingredients.

TABLE 3

| Ingredients | Comparative 2' | Accord E | Accord F | Accord G |
| --- | --- | --- | --- | --- |
| oxydibenzene, % | 1.59 | 2.64 | 3.69 | 4.74 |
| ethyl 2-methylbutanoate, % | 0.53 | 0.88 | 1.23 | 1.58 |
| 1,3,3-trimethyl-2-oxabicyclo[2.2.2]octane, % | 0.53 | 0.88 | 1.23 | 1.58 |
| 1-(5,5-dimethylcyclohex-1-en-1-yl)pent-4-en-1-one, % | 0.53 | 0.88 | 1.23 | 1.58 |
| 4,6-dimethylcyclohex-3-enecarbaldehyde, % | 1.8 | 1.69 | 1.74 | 1.69 |
| Total Class 1, % | 5 | 7 | 9 | 11 |

Speed of Diffusivity

Following the protocol described above, the speeds of diffusivity of Accords E, F, G, and Comparative 2' were measured.

Accords E, F, and G each had a speed of diffusivity of 2.88, 2.72, and 2.81 seconds. Comparative 2' had a speed of diffusivity of 3.2 seconds.

Examples 9 and 10

Fragrance E of this invention was prepared by adding 11% of Accord E to a model fragrance Ariel Sunrise (commercially available from IFF, Hilversum, the Netherlands). Fragrance Ariel Sunrise contained 4.2% of Class 1 ingredients. Fragrance E contained 5% of Class 1 ingredients.

Powder Detergent Composition E of this invention was prepared by adding 0.1% of Fragrance E to an unscented model powder detergent. Comparative Detergent 4' was prepared by adding 0.1% of fragrance Ariel Sunrise instead of Fragrance E.

Fragrance intensity and speed of diffusivity were evaluated. Composition E had a fragrance intensity of 22.55 and a speed of diffusivity of 2.33 seconds. Comparative Detergent 4' had a fragrance intensity of 17.87 and a speed of diffusivity of 2.81 seconds.

Example 11

Fragrance F of this invention was prepared by adding 7% of Accord F to Ariel Sunrise to have 5.73% of Class 1 ingredient.

Each of Fragrance F and Ariel Sunrise was added to an unscented model liquid detergent at 1%. The liquid detergent containing Fragrance F had a faster bloom scent than the liquid detergent containing Ariel Sunrise.

Each of Fragrance F and Ariel Sunrise was also added to an unscented fabric conditioner at 1%. Fragrance F showed improved speed of bloom and intensity as compared to Ariel Sunrise.

Example 12

Fragrance FA of this invention was prepared by mixing a model fragrance Thunder (commercially available from IFF, Hilversum, the Netherlands). Fragrance FA contained 8.3% of Class 1 ingredients. Fragrance Thunder contained 5.3% of Class 1 ingredients.

Microcapsule FA was prepared following the procedure described in EP 1 797 946 B1 using Fragrance FA.

Comparative Microcapsule 4' was prepared following the same procedure except that fragrance Thunder was used.

Both microcapsules were evaluated in a liquid detergent laundry application.

Microcapsule FA showed improved speed of bloom and also fragrance intensity over Comparative Microcapsule 4'.

Examples 13-20

Four fragrance accords of this invention, Accords I, J, K, and L, were prepared using various amounts of Class 1 ingredients.

Accord I contained 10.2 wt % of Class 1 ingredients (e.g. 1,3,3-trimethyl-2-oxabicyclo[2.2.2]octane, ethyl 2-methylbutanoate, methyl 2-aminobenzoate, 1-methyl-4-(prop-1-en-2-yl)cyclohex-1-ene, (2R,4S)-4-methyl-2-(2-methylprop-1-en-1-yl)tetrahydro-2H-pyran, methyl benzoate and 1-methoxy-4-methylbenzene) and 9.8 wt % of Class 2 ingredients.

Accord J contained 54 wt % of Class 1 ingredients (e.g. ethyl 2-methylbutanoate, 1-(5,5-dimethylcyclohex-1-en-1-yl)pent-4-en-1-one) and 10 wt % of Class 2 ingredients.

Accord K contained 10.2 wt % of Class 1 ingredients (e.g. oxydibenzene, ethyl hexanoate, 1-(5,5-dimethylcyclohex-1-en-1-yl)pent-4-en-1-one, 2-(3-phenylpropyl)pyridine, (2R,4S)-4-methyl-2-(2-methylprop-1-en-1-yl)tetrahydro-2H-pyran, methyl 2-aminobenzoate, (1R,2R,4R)-ethyl bicyclo[2.2.1]hept-5-ene-2-carboxylate, 4-methylene-2-phenyltetrahydro-2H-pyran) and 10 wt % of Class 2 ingredients.

Accord L contained 46 wt % of Class 1 ingredients (e.g. oxydibenzene, (2R,4S)-4-methyl-2-(2-methylprop-1-en-1-yl)tetrahydro-2H-pyran, 4-methylene-2-phenyltetrahydro-2H-pyran) and 22.2 wt % of Class 2 ingredients.

Four fragrances of this invention, i.e., Fragrances I-L, were prepared using fragrance Happy Luxury or Healthy Life (both fragrances commercially available from International Flavors & Fragrances, Union Beach, N.J.). Fragrance Happy Luxury contained 0.1 wt % of Class 1 ingredients and 12.95 wt % of Class 2 ingredients. Fragrance Healthy Life contained 2.6 wt % of Class 1 ingredients and 6.1 wt % of Class 2 ingredients.

Fragrances I and J were prepared by mixing 80 wt % of Happy Luxury and 20 wt % of Accord I or Accord J, respectively.

Fragrances K and L were prepared by mixing 80 wt % of Healthy Life and 20 wt % of Accord K or Accord L, respectively.

Each of fragrances I-L was separated added at 1 wt % neat oil in an IFF palm base bar soap. The bar soaps were aged for 7 days prior sensory test.

Both fragrances Happy Luxury and Healthy Life were used as controls.

The soap bars were evaluated for bloom fragrance intensity by a panel of trained judges at a scale of 0-100. A score of 5 or less indicates that the fragrance or ingredient has a weak smell. A score of 15 indicates a moderate smell. A score of 35 indicates a strong smell.

The bloom fragrance intensity results are shown in Table 4 below.

TABLE 4

| Fragrance | Bloom score |
| --- | --- |
| Fragrance I | 24.59 |
| Fragrance J | 25.54 |
| Happy Luxury | 19.33 |
| Fragrance I | 23.99 |
| Fragrance J | 24.44 |
| Happy Luxury | 19.46 |

Examples 21-24

Four fragrances of this invention, i.e., Fragrances M, N, O, and P, were prepared using fragrance Solitaire (commercially available from International Flavors & Fragrances, Union Beach, N.J.). Fragrance Solitaire contained 0.14 wt % of Class 1 ingredients and 16.8 wt % of Class 2 ingredients.

Each of Fragrances M-P were prepared by mixing 95 wt % of Solitaire and 5 wt % of Accord I, J, K, or L, respectively. Fragrance Solitaire was used as controls.

Each of the four fragrances was added to a model shower gel at a level of 1.5 wt %, The shower gels were evaluated for bloom fragrance intensity by a panel of trained judges at a scale of 0-100. A score of 15 or less indicates that the fragrance or ingredient has a weak smell. A score from 20 to 40 indicates a medium smell. A score of above 40 indicates a strong smell.

The bloom fragrance intensity results are shown in Table 5 below.

TABLE 5

| Fragrance | Bloom score |
| --- | --- |
| M | 21.93 |
| N | 21.26 |
| O | 23.48 |
| P | 22.96 |
| SOLITAIRE | 18.16 |

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Indeed, to achieve the purpose of designing a high performing bloom fragrance accord or composition, one skilled in the art can choose different ingredients and varying their concentrations.

From the above description, a skilled artisan can easily ascertain the essential characteristics of the present invention, and without departing from the spirit and scope thereof, can make various changes and modifications of the invention to adapt it to various usages and conditions.

What is claimed is:

1. A fragrance accord comprising:
   (i) at least 7 wt % of one or more Class 1 fragrance ingredients, and
   (ii) 5 to 93 wt % of one or more Class 2 fragrance ingredients,
wherein
   each of the Class 1 fragrance ingredients has an experimental velocity of 8.5 cm/second or greater and is selected from the group consisting of

| Ingredient | CAS No. |
|---|---|
| oxydibenzene | 101-84-8 |
| 1,3,3-trimethyl-2-oxabicyclo[2.2.2]octane | 470-82-6 |
| (2R,4S)-2-methyl-4-propyl-1,3-oxathiane | 59323-76-1 |
| ethyl 2-methylbutanoate | 7452-79-1 |
| (2R,4S)-4-methyl-2-(2-methylprop-1-en-1-yl)tetrahydro-2H-pyran | 3033-23-6 |
| 1-methyl-4-(prop-1-en-2-yl)cyclohex-1-ene | 138-86-3 |
| (1R,2R,4R)-ethyl bicyclo[2.2.1]hept-5-ene-2-carboxylate | — |
| 2-isobutylthiazole | 18640-74-9 |
| 4-methylene-2-phenyltetrahydro-2H-pyran | 60335-74-2 |
| ethyl hexanoate | 123-66-0 |
| 1-(5,5-dimethylcyclohex-1-en-1-yl)pent-4-en-1-one | 56973-85-4 |
| 4,6-dimethylcyclohex-3-enecarbaldehyde | 36635-35-5 |
| methyl benzoate | 93-58-3 |
| 2-isopropyl-4-methylthiazole | 15679-13-7 |
| 1-methoxy-4-methylbenzene | 104-93-8 |
| ethyl 2-methylpentanoate | 39255-32-8 |
| 1-methyl-4-(prop-1-en-2-yl)cyclohex-1-ene | 138-86-3 |
| 2-isobutyl-3-methoxypyrazine | 24683-00-9 |
| 2-(3-phenylpropyl)pyridine | 2110-18-1 |
| (2-methoxyethyl)benzene | 3558-60-9 |
| 2,6,6-trimethylbicyclo[3.1.1]hept-2-ene | 80-56-8 |
| methyl 2-aminobenzoate | 134-20-3 |
| Cypress oil | 84696-07-1 |
| (3aR,8bS)-2,2,6,6,7,8,8-heptamethyldecahydro-2H-indeno[4,5-b]furan | — |
| 1-(3-methylbenzofuran-2-yl)ethan-1-one | 23911-56-0, | and
each of the Class 2 fragrance ingredients has an experimental velocity of less than 8.5 cm/second and greater than 5 cm/second and is selected from the group consisting of

| Ingredients | CAS No. |
|---|---|
| (E)-4-(2,6,6-trimethylcyclohex-2-en-1-yl)but-3-en-2-one | 31798-11-5 |
| 1-methyl-4-(propan-2-ylidene)cyclohex-1-ene | 586-62-9 |
| (2Z,6Z)-3,7-dimethylnona-2,6-dienenitrile | 61792-11-8 |
| octanal | 124-13-0 |
| 2,6-dimethylhept-5-enal | 106-72-9 |
| (1S,2R)-2,4-dimethylcyclohex-3-ene-1-carbaldehyde | 188716-52-1 |
| (E)-dec-6-enal | — |
| (Z)-hex-3-en-1-yl methyl carbonate | 67633-96-9 |
| (E)-4-(2,6,6-trimethylcyclohex-1-en-1-yl)but-3-en-2-one | 79-77-6 |
| methyl 2-methylbenzoate | 89-71-4 |
| 2-pentylcyclopentan-1-one | 4819-67-4 |
| 4-phenylbutan-2-one | 2550-26-7 |
| 1-methyl-4-(prop-1-en-2-yl)cyclohex-1-ene | 138-86-3 |
| Pine super xtreme | — |
| (E)-4-methyldec-3-en-5-ol | 81782-77-6 |
| cinnamaldehyde | 14371-10-9 |
| (1R,2R,4R)-1,7,7-trimethylbicyclo[2.2.1]heptan-2-ol | 124-76-5 |
| (Z)-hex-3-en-1-ol | 928-96-1 |
| 2-isopropyl-5-methylphenol | 89-83-8 |
| (E)-undec-9-enal | 143-14-6 |
| 2-methoxynaphthalene | 93-04-9 |
| 1,1'-oxybis(propan-2-ol) | 110-98-5 |
| (1S,2S)-2-(tert-butyl)cyclohexan-1-ol | 7214-18-8 |
| 8-isopropyl-6-methylbicyclo[2.2.2]oct-5-ene-2-carbaldehyde | 68259-31-4 |
| dodecanal | 112-54-9 |
| p-tolyl acetate | 140-39-6 |
| 1H-indole | 120-72-9 |
| 3,7-dimethylocta-1,6-dien-3-yl acetate | 115-95-7 |
| 3,7-dimethyloct-6-enenitrile | 51566-62-2 |
| dodecanenitrile | 2437-25-4 |
| (2-(1-propoxyethoxy)ethyl)benzene | 7493-57-4 |
| 3-methyl-2-pentylcyclopent-2-en-1-one | 1128-08-1 |
| 2,2,5,8,8,9a-hexamethyloctahydro-3aH-4a,9-methanoazuleno[5,6-d][1,3]dioxole | 211299-54-6 |
| 3a,4,5,6,7,7a-hexahydro-1H-4,7-methanoinden-5-yl propionate | 67634-24-6 |
| 3-(4-methylcyclohex-3-en-1-yl)butanal | 6784-13-0 |
| (2Z,6Z)-3,7-dimethylnona-2,6-dienenitrile | 61792-11-8 |
| 3,7-dimethylocta-1,6-dien-3-ol | 126-91-0 |
| 2,6,6-trimethylbicyclo[3.1.1]hept-2-ene | 80-56-8 |
| 3-(4-(tert-butyl)phenyl)-2-methylpropanal | 80-54-6 |
| (E)-3-methyl-5-(2,2,3-trimethylcyclopent-3-en-1-yl)pent-4-en-2-ol | 67801-20-1 |
| (E)-1-methoxy-4-(prop-1-en-1-yl)benzene | 4180-23-8 |
| (E)-tridec-2-enenitrile | 22629-49-8 |
| (E)-3-methyl-4-(2,6,6-trimethylcyclohex-2-en-1-yl)but-3-en-2-one | 127-51-5 |
| 3-(4-ethylphenyl)-2,2-dimethylpropanal | 67634-15-5 |
| (E)-trideca-3,12-dienenitrile | 134769-33-8 |
| 2-ethoxy-4-methylphenol | 2563-07-7 |
| benzaldehyde | 100-52-7 |
| 3-methylbenzofuran-5-ol | 7182-21-0 |
| hexanal | 66-25-1 |
| 3a,4,5,6,7,7a-hexahydro-1H-4,7-methanoinden-5-yl isobutyrate | 67634-20-2 |
| 2-((3aR,4S,5R,7S,7aR)-octahydro-1H-4,7-methanoinden-5-yl)acetaldehyde | 1339119-15-1 |
| Freshness Green SUB/accord | — |
| 3,5,5-trimethylhexanal | 5435-64-3 |
| 4-methoxybenzaldehyde | 123-11-5 |
| ethyl isobutyrate | 97-62-1 |
| (E)-3,7-dimethylocta-2,6-dien-1-yl formate | 105-86-2 |
| 1-methyl-4-(prop-1-en-2-yl)cyclohex-1-ene | 138-86-3 |
| (E)-3,3-dimethyl-5-(2,2,3-trimethylcyclopent-3-en-1-yl)pent-4-en-2-ol | 107898-54-4 |
| 3,7-dimethyloct-6-en-1-yl acetate | 150-84-5 |
| 4-allyl-2-methoxyphenol | 97-53-0 |
| (3a5,4R,75,7aR)-octahydro-1H-4,7-methanoindene-1-carbaldehyde | 30772-79-3 |
| 1,1'-oxybis(propan-2-ol) | 110-98-5 |
| ROSEMARY OIL | 84604-14-8 |
| 8-methyl-1-oxaspiro(4.5)decan-2-one | 94201-19-1 |
| 2-cyclohexyl-1,6-heptadien-3-one | 313973-37-4. |

2. The fragrance accord of claim 1, where in the Class 1 fragrance ingredients each have a kinetic energy of more than 5000 joules and the Class 2 fragrance ingredients each have a kinetic energy of 1400 to 5000 joules.

3. The fragrance accord of claim 1, further comprising one or more malodor counteractive agents, or one or more antibacterial agents.

4. The fragrance accord of claim 1, further comprising one or more Class 3 fragrance ingredients, each of which has an experimental velocity of 5 cm/second or less, wherein the sum of the Class 1 fragrance ingredients, the Class 2 fragrance ingredients, and the Class 3 fragrance ingredients is 100%.

5. The fragrance accord of claim 1, further comprising an essential oil.

6. The fragrance accord of claim 1, wherein the fragrance accord comprises at least 8 wt % of two or more Class 1 fragrance ingredients.

7. The fragrance accord of claim 1, wherein the fragrance accord comprises at least five Class 1 fragrance ingredients.

8. The fragrance accord of claim 1, wherein the fragrance accord comprised 5 to 70 wt % of the Class 2 fragrance ingredients.

9. The fragrance accord of claim 1, wherein the fragrance accord comprises 20 to 100 wt % of the Class 1 and Class 2 fragrance ingredients.

10. The fragrance accord of claim 1, wherein the fragrance accord has a fragrance intensity index of at least 0.5.

11. A delivery system comprising a fragrance accord of claim 1.

12. A consumer product comprising a fragrance accord of claim 1.

13. The consumer product of claim 12, wherein the fragrance accord is dosed at a level of 0.005 to 10% by weight of the consumer product.

14. The consumer product of claim 12, wherein the consumer product is a shampoo, a hair conditioner, a hair rinse, a hair refresher, a hair fixative or styling aid, a hair bleach, a hair dye or colorant, a bar soap, a body wash, a cosmetic preparation, an all-purpose cleaner, a bathroom cleaner, a floor cleaner, a window cleaner, a bath tissue, a paper towel, a disposable wipe, a diaper rash cream or balm, a baby powder, a diaper, a bib, a baby wipe, an oral care product, a tooth paste, an oral rinse, a tooth whitener, a denture adhesive, a hand sanitizer, an anti-inflammatory balm, an anti-inflammatory ointment, an anti-inflammatory spray, a health care device, a dental floss, a toothbrush, a tampon, a feminine napkin, a personal care product, a sunscreen lotion, a sunscreen spray, a wax-based deodorant, a glycol type deodorant, a soap type deodorant, a facial lotion, a body lotion, a hand lotion, a body powder, a shave cream, a bath soak, an exfoliating scrib, a foot cream, a facial tissue, a cleansing wipe, a fabric care product, a fabric softener, a fabric refresher, an ironing water, a liquid laundry detergent, a powder laundry detergent, a liquid dish detergent, an automatic dish detergent, a unit dose tablet or capsule, a scent booster, a drier sheet, a fine fragrance, a solid perfume, eau de parfum, parfum, cologne, alcohol free perfume, perfume powder, perfume wax, perfume emulsion, a powder foundation, a liquid foundation, an eye shadow, a lipstick or lip balm, an Eau De Toilette product, a deodorant, a rug deodorizer, a candle, a room deodorizer, a disinfectant, a bleach, an aerosol antiperspirant, a stick antiperspirant, a roll-on antiperspirant, an emulsion spray antiperspirant, a clear emulsion stick antiperspirant, a soft solid antiperspirant, an emulsion roll-on antiperspirant, a clear emulsion stick antiperspirant, an opaque emulsion stick antiperspirant, a clear gel antiperspirant, a clear stick deodorant, a spray deodorant, a perfume gel, a perfume emulsion, a perfume cream, a perfume oil, a wax, a hair perfume, a cloth perfume, a deodorant perfume, a foaming bath, a bath oil, a bath salt, a bath sachet, a bath crystal, a bath tablet, a perfume jewel, a perfumed polymer, or a fragrance composition for digital devices.

15. The consumer product of claim 12, wherein the fragrance accord is dosed at a level of 0.01 to 0.5% by weight of the consumer product, and the consumer product is a shampoo, a hair conditioner, a bar soap, a body wash, an all-purpose cleaner, a fabric conditioner, a liquid laundry detergent, or a powder laundry detergent.

16. A fragrance composition comprising 5 wt % or more of a fragrance accord of claim 1.

\* \* \* \* \*